United States Patent [19]
Sprecher et al.

[11] Patent Number: 5,935,854
[45] Date of Patent: Aug. 10, 1999

[54] HUMAN AMYLOID PROTEIN PRECURSOR HOMOLOG AND KUNITZ-TYPE INHIBITOR

[75] Inventors: Cindy A. Sprecher; Donald C. Foster, both of Seattle, Wash.; Kjeld E. Norris, Hellerup, Denmark

[73] Assignee: ZymoGenetics, Inc., Seattle, Wash.

[21] Appl. No.: 08/424,017

[22] Filed: Apr. 18, 1995

Related U.S. Application Data

[60] Division of application No. 08/155,331, Nov. 19, 1993, Pat. No. 5,441,931, which is a continuation-in-part of application No. 07/985,692, Dec. 2, 1992, Pat. No. 5,436,153.

[51] Int. Cl.$^6$ ........................................... C12N 5/00
[52] U.S. Cl. .................... 435/331; 530/387.9; 530/388.1
[58] Field of Search .............................. 530/387.9, 388.1, 530/388.24; 435/240.26, 326, 331, 335

[56] References Cited

FOREIGN PATENT DOCUMENTS

| 0386752 | 12/1990 | European Pat. Off. ........ C12H 15/18 |
| 586 790 A1 | 3/1994 | European Pat. Off. . |
| 90/14841 | 12/1990 | WIPO . |
| 93/14200 | 7/1993 | WIPO . |

OTHER PUBLICATIONS

Palmert, M.R. et al. 1988. Biochem. Biophys. Res. Comm. 156: 432–437.

Palmert, M.R. et al. 1989. Proc. Natl. Acad. Sci. USA 86: 6338–6342.

Weidermann, A. et al. 1989. Cell 57: 115–126.

Hyman, B.T. et al. 1992 (Jan.) J. Neuropathology & Experimental Neurology 51: 76–83.

Yan et al., *Proc. Natl. Acad. Sci. USA 87*: 2405–2408, 1990.

Bram et al., *Mol. Cell. Biol.* 7(1): 403–409, 1987.

Sprecher et al., *Biochem. 32*: 4481–4486, 1993.

Kido et al., *Biochemical and Biophysical Research Communications 167*(2): 716–721, 1990.

Holtzman et al., *TIBS 16*: 140–144, 1991.

Wasco et al., *Nature Genetics 5*: 95–99, 1993.

*Primary Examiner*—Sheela Huff
*Attorney, Agent, or Firm*—Jennifer K. Johnson; Paul G. Lunn, Esq.

[57] ABSTRACT

The present invention provides isolated DNA molecules comprising a DNA segment encoding a novel human amyloid protein precursor homologue and novel Kunitz-type inhibitors. Also provided are DNA constructs comprising a first DNA segment encoding a novel human amyloid protein precursor homologue or a novel Kunitz-type inhibitor wherein said first DNA segment is operably linked to additional DNA segments required for the expression for the first DNA segment, as well as host cells containing such DNA constructs and methods for producing proteins from the host cells.

7 Claims, No Drawings

HUMAN AMYLOID PROTEIN PRECURSOR HOMOLOG AND KUNITZ-TYPE INHIBITOR

CROSS REFERENCE TO RELATED APPLICATIONS

This application is a divisional application of U.S. Ser. No. 08/155,331 filed Nov. 19, 1993, now U.S. Pat. No. 5,441,931 which is a continuation-in-part application of Ser. No. 07/985,692 filed Dec. 2, 1992, now U.S. Pat. No. 5,436,153.

BACKGROUND OF THE INVENTION

Polymorphonuclear leukocytes (neutrophils or PMNs) and mononuclear phagocytes (monocytes) play an important part in tissue injury, infection, acute and chronic inflammation and wound healing. There is some indication that a number of chronic diseases are caused by pathological proteolysis due to overstimulation of the PMNs. Such overstimulation may be caused by, for instance, autoimmune response, chronic infection, tobacco smoke or other irritants, etc.

PMNs migrate from the blood to the site of inflammation and, following appropriate stimulation, they release oxidant compounds ($O_2$, $O_2^-$, $H_2O_2$ and HOCl) as well as granules containing a variety of proteolytic enzymes. The secretory granules contain, inter alia, alkaline phosphatase; metalloproteinases such as gelatinase and collagenase; and serine proteases such as neutrophil elastase, cathepsin G and proteinase-3.

Latent metalloproteinases are released together with tissue inhibitor of metalloproteinase (TIMP). The activation mechanism has not been fully elucidated, but it is likely that oxidation of thiol groups and/or proteolysis play a part in the process. Also, free metalloproteinase activity is dependent on inactivation of TIMP.

PMNs contain large quantities of serine proteases, and about 200 mg of each of the leukocyte proteases are released daily to deal with invasive agents in the body. Acute inflammation leads to a many-fold increase in the amount of enzyme released. In the azurophil granules of polymorphonuclear leukocytes, the serine proteases neutrophil elastase, cathepsin G and proteinase-3 are packed as active enzymes complexed with glucosaminoglycans. These complexes are inactive but dissociate on secretion to release the active enzymes. Under normal conditions, proteolysis is kept at an acceptably low level by large amounts of the inhibitors $\alpha_1$-proteinase inhibitor ($\alpha_1$-PI), $\alpha_1$-chymotrypsin inhibitor ($\alpha_1$-ChI) and $\alpha_2$ macroglobulin that are found in plasma. However, the PMNs are able to inactivate the inhibitors locally. Thus, $\alpha_1$-PI, which is the most important inhibitor of neutrophil elastase, is sensitive to oxidation at the reactive center (Met-358) by oxygen metabolites produced by stimulated PMNs. This reduces the affinity of $\alpha_1$-PI for neutrophil elastase by approximately 2000 times.

After local neutralization of $\alpha_1$-PI, the neutrophil elastase is able to degrade a number of inhibitors of other proteolytic enzymes. Neutrophil elastase cleaves $\alpha_1$-ChI and thereby promotes cathepsin G activity. It also cleaves TIMP, resulting in tissue degradation by metalloproteinases. Furthermore, neutrophil elastase cleaves antithrombin III, heparin cofactor II, and tissue factor pathway inhibitor (TFPI), which probably promotes clot formation. On the other hand, the ability of neutrophil elastase to degrade coagulation factors is assumed to have the opposite effect, such that the total effect of neutrophil elastase is unclear. The effect of neutrophil elastase on fibrinolysis is less ambiguous. Fibrinolytic activity increases when neutrophil elastase cleaves plasminogen activator inhibitor and $\alpha_2$ plasmin inhibitor. Furthermore, both of these inhibitors are oxidized and inactivated by $O_2$ metabolites.

Proteinase inhibitors are classified into a series of families based on extensive sequence homologies among the family members and the conservation of intrachain disulfide bridges (for review, see Laskowski and Kato, Ann. Rev. Biochem. 49: 593–626, 1980). Serine protease inhibitors of the Kunitz family are characterized by their homology with aprotinin (bovine pancreatic trypsin inhibitor). Aprotinin is known to inhibit various serine proteases including trypsin, chymotrypsin, plasmin and kallikrein. Kunitz-type inhibitor domains have been reported in larger proteins such as the inter-α-trypsin inhibitors (Hochstrasser et al., Hoppe-Seylers Z. Physiol. Chem. 357: 1659–1661, 1969 and Tschesche et al., Eur. J. Biochem. 16: 187–198, 1970) and the β-amyloid protein precursor. The β-amyloid protein precursor (APP) contains an approximately 40 amino acid fragment that forms the senile plaques observed in Alzheimer's patients, patients with Down's syndrome and in aged normal patients. The gene encoding APP yields three alternatively spliced mRNAs, two of which have been demonstrated to encode Kunitz-type inhibitor domains (see Ponte et al., Nature 331: 525–528, 1988; Tanzi et al., Nature 331: 528–530, 1988 and Kitaguchi et al., Nature 331: 530–532, 1988). In addition to the Kunitz-type inhibitor domain, each protein precursor contains a signal peptide, a cysteine-rich region, a highly negatively charged region, a transmembrane domain and an intracellular domain (see Kitaguchi et al. ibid.).

Of the Kunitz-type inhibitors, aprotinin is used therapeutically in the treatment of acute pancreatitis, various states of shock syndrome, hyperfibrinolytic hemorrhage and myocardial infarction (see, for example, Trapnell et al., Brit. J. Surg. 61: 177, 1974; McMichan et al., Circulatory shock 9: 107, 1982; Auer et al., Acta Neurochir. 49: 207, 1979; Sher, Am. J. Obstet. Gynecol. 129: 164, 1977; and Schneider, Artzneim.-Forsch. 26: 1606, 1976). Administration of aprotinin in high doses significantly reduces blood loss in connection with cardiac surgery, including cardiopulmonary bypass operations (see, for example, Bidstrup et al., J. Thorac. Cardiovasc. Surg. 97: 364–372, 1989; van Oeveren et al., Ann. Thorac. Surg. 44: 640–645, 1987). It has previously been demonstrated (Wenzel and Tschesche, Angew. Chem. Internat. Ed. 20: 295, 1981) that certain aprotinin analogs, e.g. aprotinin (1–58, Val15), exhibit a relatively high selectivity for granulocyte elastase and an inhibitory effect on collagenase. Aprotinin (1–58, Ala15) has a weak effect on elastase, while aprotinin (3–58, Arg15, Ala17, Ser42) exhibits an excellent plasma kallikrein inhibitory effect (WO 89/10374).

However, when administered in vivo, aprotinin has been found to have a nephrotoxic effect in rats, rabbits and dogs after repeated injections of relatively high doses (Bayer, Trasylol, Inhibitor of Proteinase; Glaser et al. in "Verhandlungen der Deutschen Gesellschaft fur Innere Medizin, 78. Kongress," Bergmann, Munich, 1972, pp. 1612–1614). The nephrotoxicity (appearing, i.e., in the form of lesions) observed for aprotinin might be ascribed to the accumulation of aprotinin in the proximal tubulus cells of the kidneys as a result of the high positive net charge of aprotinin, which causes it to be bound to the negatively charged surfaces of the tubuli. This nephrotoxicity makes aprotinin less suitable for clinical purposes, particularly in those uses requiring administration of large doses of the inhibitor (such as cardiopulmonary bypass operations). Furthermore, aprotinin is a bovine protein, which may induce an immune response upon administration to humans.

It is therefore an object of the present invention to provide novel human protease inhibitors of the Kunitz family of inhibitors with similar inhibitor profiles for use in the treatment of acute pancreatitis, various states of shock syndrome, hyperfibrinolytic hemorrhage and myocardial infarction. It is further an object of the present invention to provide novel amyloid protein precursor homologues for use in studying the relative levels of the precursor in patients exhibiting Alzheimer's disease and to identify patients with mutations in the protein precursor.

SUMMARY OF THE INVENTION

Briefly stated, the present invention provides novel isolated DNA molecules encoding human amyloid protein precursor homologues and human Kunitz-type inhibitors. Within one embodiment of the invention, the DNA molecule comprises a DNA segment encoding a human amyloid protein precursor homologue, wherein the DNA segment comprises the sequence of nucleotides of SEQ ID NO:12 from nucleotide 73 to nucleotide 2361. Within another embodiment, the DNA segment encodes a human amyloid protein precursor homologue comprising the amino acid sequence of SEQ ID NO:13 from methionine, amino acid number 1, to isoleucine, amino acid number 763. Also provided are DNA constructs comprising a first DNA segment encoding a human amyloid protein precursor homologue operably linked to additional DNA segments necessary for the expression of the first DNA segment, host cells containing such DNA constructs, as well as methods for producing a human amyloid protein precursor homologue comprising the step of culturing a host cell under conditions promoting the expression of a DNA segment encoding a human amyloid precursor protein homologue.

Within another aspect of the invention, DNA molecules are provided which comprise a DNA segment encoding a human Kunitz-type inhibitor, wherein the DNA segment comprises the sequence of nucleotides of SEQ ID NO:1 from nucleotide 171 to nucleotide 331 or the sequence of nucleotides of SEQ ID NO:1 from nucleotide 159 to nucleotide 331. Within another embodiment, the DNA segment encodes a human Kunitz-type inhibitor comprising the amino acid sequence of SEQ ID NO:2 from alanine, amino acid 56 to alanine, amino acid number 110; the amino acid sequence of SEQ ID NO:2 from aspartic acid, amino acid number 53 to alanine, amino acid number 110; or the amino acid sequence of SEQ ID NO:2 from valine, amino acid number 57 to alanine, amino acid number 110 and which further contains a glutamic acid residue on the amino terminus. Also provided are DNA constructs comprising a first DNA segment encoding a human Kunitz-type inhibitor operably linked to additional DNA segments necessary for the expression of the first DNA segment, host cells containing such DNA constructs, as well as methods for producing a human Kunitz-type inhibitor comprising the step of culturing a host cell under conditions promoting the expression of a DNA segment encoding a human Kunitz-type inhibitor.

Within another aspect of the invention, isolated amyloid protein precursor homologues and Kunitz-type inhibitors are provided. Within one embodiment, an isolated amyloid protein precursor homologue comprises the amino acid sequence of SEQ ID NO:13 from methionine, amino acid number 1, to isoleucine, amino acid number 763. Within another embodiment, an isolated human Kunitz-type inhibitor comprises the amino acid sequence of SEQ ID NO:2 from alanine, amino acid 56 to alanine, amino acid number 110; the amino acid sequence of SEQ ID NO:2 from aspartic acid, amino acid number 53 to alanine, amino acid number 110; or the amino acid sequence of SEQ ID NO:2 from valine, amino acid number 57 to alanine, amino acid number 110 and which further contains a glutamic acid residue on the amino terminus.

Within another aspect of the invention, isolated antibodies are provided which specifically bind to a human amyloid protein precursor or to a human Kunitz-type inhibitor. Within one embodiment, the antibody is a monoclonal antibody.

Within yet another aspect of the invention, a pharmaceutical composition is provided which comprises a human Kunitz-type inhibitor comprising the amino acid sequence of SEQ ID NO:2 from alanine, amino acid 56 to alanine, amino acid number 110; the amino acid sequence of SEQ ID NO:2 from aspartic acid, amino acid number 53 to alanine, amino acid number 110; or the amino acid sequence of SEQ ID NO:2 from valine, amino acid number 57 to alanine, amino acid number 110 and which further contains a glutamic acid residue on the amino terminus.

Within another aspect of the invention, probes of at least 12 nucleotides are provided, wherein the probes are capable of hybridizing with nucleic acids encoding a human amyloid protein precursor homologue comprising the nucleotide sequence of SEQ ID NO:12, nucleotide variants of SEQ ID NO:12, or DNA segments encoding DNA sequences complementary to SEQ ID NO:12 or its variants. Within yet another aspect of the invention, probes of at least 12 nucleotides are provided wherein the probes are capable of hybridizing with nucleic acids encoding a Kunitz-type inhibitor domain comprising the nucleotide sequence of SEQ ID NO:1, nucleotide variants of SEQ ID NO:1, or DNA segments encoding DNA sequences complementary to SEQ ID NO:1 or its variants.

These and other aspects will become evident upon reference to the following detailed description.

DETAILED DESCRIPTION OF THE INVENTION

The present invention provides a novel human amyloid protein precursor homologue containing a protease inhibitor domain that shares homology with the Kunitz family of protease inhibitors and a novel placental kunitz-type inhibitor. One advantage of the inhibitors of the present invention is that, contrary to aprotinin, the inhibitors of the present invention are human proteins, so that undesired immunological reactions on administration to humans are significantly reduced. The Kunitz-type inhibitor of the amyloid protein precursor homologue has the advantage that it has a negative net charge as opposed to aprotinin, which may thereby reduce the risk of kidney damage on administration of large doses of the inhibitor. The amyloid protein precursor homologues of the present invention and the DNA sequences encoding such proteins provide the advantage of allowing the expression of such proteins in patients with Alzheimer's disease to be compared with the expression of such protein in normal patients.

Features of the present invention include isolated DNA molecules encoding novel human Kunitz-type inhibitors. Another feature of the present invention is an isolated DNA molecule encoding a human amyloid protein precursor homologue. Such isolated molecules are those that are separated from their natural environment and include cDNA and genomic clones. Isolated DNA molecules of the present invention are provided free of other genes with which they are naturally associated and may include naturally occurring 5' and 3' untranslated sequences that represent regulatory regions such as promoters and terminators. The identification of regulatory regions within the naturally occurring 5' and 3' untranslated regions will be evident to one of ordinary skill in the art (for review, see Dynan and Tijan, *Nature* 316: 774–778, 1985; Birnstiel et al., Cell 41: 349–359, 1985; Proudfoot, *Trends in Biochem. Sci.* 14: 105–110, 1989; and Sambrook et al., *Molecular Cloning: A Laboratory Manual, Second Edition*, Cold Spring Harbor, N.Y., 1989; which are incorporated herein by reference).

The isolated DNA molecules of the present invention are useful in producing recombinant human Kunitz-type inhibitors and recombinant human amyloid protein precursor homologues. Thus, the present invention provides the advantage that human Kunitz-type inhibitors and amyloid protein precursor homologues are produced in high quantities that may be readily purified using methods known in the art (see generally, Scopes, Protein Purification, Springer-Verlag, N.Y., 1982). Alternatively, the proteins of the present invention can be synthesized following any suitable method, such as by exclusively solid-phase techniques (i.e., the method of Barany and Merrifield (in *The Peptides. Analysis, Synthesis, Biology* Vol. 2, Gross and Meienhofer, eds, Academic Press, N.Y., pp. 1–284, 1980)), by partial solid-phase techniques, by fragment condensation or by classical solution addition.

Kunitz-type inhibitor activity can be measured using the method essentially described by Norris et al. (*Biol. Chem. Hoppe-Seyler* 371: 37–42, 1990). Briefly, various fixed concentrations of the Kunitz-type inhibitor are incubated in the presence of serine proteases at the concentrations listed in Table 2 in 100 mM NaCl, 50 mM Tris HCl, 0.01% TWEEN80 (Polyoxyethylenesorbitan monoleate) (pH 7.4) at 25° C. After a 30 minute incubation, the residual enzymatic activity is measured by the degradation of a solution of the appropriate substrate as listed in Table 2 in assay buffer. The samples are incubated for 30 minutes after which the absorbance of each sample is measured at 405 nm. An inhibition of enzyme activity is measured as a decrease in absorbance at 405 nm or fluoresence Em at 460 nm. From the results, the apparent inhibition constant $K_i$ is calculated.

The Kunitz-type inhibitors of the present invention may be used in the disclosed methods for the treatment of, inter alia, acute pancreatitis, various states of shock syndrome, hyperfibrinolytic hemorrhage and myocardial infarction. The amyloid protein precursor homologues of the present invention may be used, inter alia, to generate antibodies for use in demonstrating tissue distribution of the precursor or for use in purifying such proteins.

Thus, an additional feature of the present invention is an isolated human Kunitz-type inhibitor or an isolated human amyloid protein precursor homologue. Isolated proteins and peptides of the present invention are proteins of at least about 50% homogeneity, more preferably of 70% to 80% homogeneity with a protein preparation of 95% to 99% or more homogeneity most preferred, particularly for pharmaceutical uses.

The present invention relates to a novel human amyloid protein precursor homologue containing a human Kunitz-type inhibitor comprising the amino acid sequence shown in Sequence ID NO:13 and/or encoded by a DNA sequence comprising the nucleotide sequence of SEQ ID NO:12. The Kunitz-type inhibitors of the present invention are up to 80 amino acids, preferably between 50 and 60 amino acids, most preferably between 53 and 57 amino acids in length and comprise the amino acid sequence shown SEQ ID NO:2 from valine, amino acid number 57 through alanine, amino acid number 110. However, as will be evident to one skilled in the art, amino-terminal and/or carboxy-terminal extensions of the Kunitz-type inhibitor may be prepared either synthetically or using recombinant DNA techniques and tested for inhibitor activity.

The DNA sequences encoding the proteins of the present invention were unexpectedly identified during screening for a cDNA corresponding to the genomic clone of an unrelated Kunitz-type inhibitor using an antisense oligonucleotide probe corresponding to a portion of the inhibitor coding sequence. Analysis of the cDNA clones revealed that the clones encoded a unique, previously unknown amyloid protein precursor homologue containing a Kunitz-type inhibitor domain and a novel placental Kunitz-type inhibitor. As used herein, the proteins of the present invention may be encoded by DNA sequences that are substantially similar to the DNA sequence disclosed herein. As used within the context of the present invention, "substantially similar" DNA sequences encompass allelic variants and genetically engineered or synthetic variants of the amyloid protein precursor homologue gene, Kunitz-type inhibitor domain of the amyloid protein precursor homologue gene, or the novel placental Kunitz-type inhibitor gene that contain conservative amino acid substitutions and/or minor additions, substitutions or deletions of amino acids. DNA sequence variants also encompass degeneracies in the DNA code wherein host-preferred codons are substituted for the analogous codons in the human sequence. In addition, substantially similar DNA sequences are those that are capable of hybridizing to the DNA sequences of the present invention under high or low stringency (see Sambrook et al., ibid.) and those sequences that are degenerate as a result of the genetic code to the amino acid sequences of the present invention. Genetically engineered variants may be obtained by using oligonucleotide-directed site-specific mutagenesis, by use of restriction endonuclease digestion and adapter ligation, or other methods well established in the literature (see for example, Sambrook et al., ibid. and Smith et al., *Genetic Engineering: Principles and Methods*, Plenum Press, 1981; which are incorporated herein by reference).

DNA sequences of the present invention may be isolated using standard cloning methods such as those described by Maniatis et al. (*Molecular Cloning: A Laboratory Manual*, Cold Spring Harbor, N.Y., 1982; which is incorporated herein by reference), Sambrook et al. (*Molecular Cloning: A Laboratory Manual, Second Edition*, Cold Spring Harbor, N.Y., 1989; which is incorporated herein by reference) or Mullis (U.S. Pat. No. 4,683,195; incorporated herein by reference). Alternatively, the coding sequences of the present invention may be synthesized using standard techniques that are well known in the art, such as by synthesis on an automated DNA synthesizer. As will be discussed in more detail below, a novel human amyloid protein precursor homologue containing a Kunitz-type inhibitor domain was identified as a 3.5 kb cDNA insert and comprises the DNA sequence of SEQ ID NO:12. In a preferred embodiment, DNA sequences encoding Kunitz-type inhibitors are obtained by PCR amplification using primers designed from SEQ ID NO:1 or its complement.

DNA molecules of the present invention or portions thereof may be used, for example, to directly detect amyloid protein precursor homologue sequences in cells. The DNA molecules of the present invention may also be used to detect kunitz-inhibitor sequences in cells. Such DNA molecules are generally synthetic oligonucleotides, but may be generated from cloned cDNA or genomic sequences and will generally comprise more than 12 nucleotides, more often from about 14 nucleotides to about 25 or more nucleotides, sometimes 40 to 60 nucleotides, and in some instances a substantial portion or even the entire amyloid protein precursor homologue gene or CDNA. The synthetic oligonucleotides of the present invention share at least about 85% identity, preferably at least 90%, and more preferably at least about 95% or more identity with a corresponding DNA sequence of the human amyloid protein precursor homologue of SEQ ID NO:12, SEQ ID NO:1 or the complement of either sequence. For use a probes, the molecules may be labeled to provide a detectable signal, such as with an enzyme, biotin, a radionuclide, fluorophore, chemiluminescer, paramagnetic particle, etc. according to methods known in the art. Probes of the present invention may be used diagnostic methods to detect cellular metabolic disorders such as thrombolic disorders.

DNA molecules used within the present invention may be labeled and used in a hybridization procedure similar to the Southern or dot blot. As will be understood by those skilled in the art, conditions that allow the DNA molecules of the present invention to hybridize to amyloid protein precursor homologue sequences or amyloid protein precursor homologue-like sequences may be determined by methods well known in the art and reviewed, for example, by Sambrook et al. (*Molecular Cloning: A Laboratory Manual, Second Edition*, Cold Spring Harbor, N.Y., 1989; which is incorporated herein by reference). Those skilled in the art will be capable of varying hybridization conditions (i.e. stringency of hybridization) of the DNA molecules as appropriate for use in the various procedures by methods well known in the literature (see, for example, Sambrook et al., ibid., pages 11.45–11.53). The higher the stringency of hybridization, the lower the number of mismatched sequences are detected. Alternatively, lower stringency will allow related sequences to be identified.

Alternatively, human amyloid protein precursor homologue sequence variants may be identified using DNA molecules of the present invention and, for example, the polymerase chain reaction (PCR) (disclosed by Saiki et al., *Science* 239: 487, 1987; Mullis et al., U.S. Pat. No. 4,686, 195; and Mullis, U.S. Pat. No. 4,683,202) to amplify DNA sequences, which are subsequently detected by their characteristic size on agarose gels or which may be sequenced to detect sequence abnormalities.

Amyloid protein precursor homologue and Kunitz-type inhibitor sequences of the present invention may be inserted into DNA constructs. As used within the context of the present invention, a DNA construct, also known as an expression vector, is understood to refer to a DNA molecule, or a clone of such a molecule, either single-or double-stranded, which has been modified through human intervention to contain segments of DNA combined and juxtaposed in a manner that would not otherwise exist in nature. DNA constructs of the present invention comprise a first DNA segment encoding an amyloid protein precursor homologue or a Kunitz-type inhibitor operably linked to additional DNA segments required for the expression of the first DNA segment. Within the context of the present invention, additional DNA segments will generally include promoters and transcription terminators, and may further include enhancers and other elements. One or more selectable markers may also be included.

In one embodiment the DNA sequence encodes a Kunitz-type inhibitor comprising the amino acid sequence of SEQ ID NO:2 from alanine, amino acid number 56 through alanine, amino acid number 110. In another embodiment, the first DNA sequence encodes a Kunitz-type inhibitor comprising the amino acid sequence of SEQ ID NO:2 from aspartic acid, amino acid 53 to alanine, amino acid 110. In yet another embodiment, the first DNA sequence encodes a Kunitz-type inhibitor comprising the amino acid sequence of SEQ ID NO:2 from valine, amino acid number 57 through alanine, amino acid number 110 and which further contains a codon for glutamic acid immediately upstream of the codon for valine, amino acid number 57.

DNA constructs may also contain DNA segments necessary to direct the secretion of a polypeptide or protein of interest. Such DNA segments may include at least one secretory signal sequence. Secretory signal sequences, also called leader sequences, prepro sequences and/or pre sequences, are amino acid sequences that act to direct the secretion of mature polypeptides or proteins from a cell. Such sequences are characterized by a core of hydrophobic amino acids and are typically (but not exclusively) found at the amino termini of newly synthesized proteins. Very often the secretory peptide is cleaved from the mature protein during secretion. Such secretory peptides contain processing sites that allow cleavage of the secretory peptides from the mature proteins as the pass through the secretory pathway. A preferred processing site is a dibasic cleavage site, such as that recognized by the *Saccharomyces cerevisiae* KEX2 gene. A particularly preferred processing site is a Lys-Arg processing site. Processing sites may be encoded within the secretory peptide or may be added to the peptide by, for example, in vitro mutagenesis.

Preferred secretory signals include the α factor signal sequence (prepro sequence: Kurjan and Herskowitz, *Cell* 30: 933–943, 1982; Kurjan et al., U.S. Pat. No. 4,546,082; Brake, EP 116,201), the PHO5 signal sequence (Beck et al., WO 86/00637), the BAR1 secretory signal sequence (MacKay et al., U.S. Pat. No. 4,613,572; MacKay, WO 87/002670), and the SUC2 signal sequence (Carlsen et al., *Molecular and Cellular Biology* 3: 439–447, 1983). Alternately, a secretory signal sequence may be synthesized according to the rules established, for example, by von Heinje (*European Journal of Biochemistry* 133: 17–21, 1983; *Journal of Molecular Biology* 184: 99–105, 1985; *Nucleic Acids Research* 14: 4683–4690, 1986). A particularly preferred signal sequence is the synthetic signal LaC212 spx (1–47)—ERLE described in WO 90/10075, which is incorporated by reference herein in its entirety.

Secretory signal sequences may be used singly or may be combined. For example, a first secretory signal sequence may be used in combination with a sequence encoding the third domain of barrier (described in U.S. Pat. No. 5,037, 243, which is incorporated by reference herein in its entirety) . The third domain of barrier may be positioned in proper reading frame 3' of the DNA segment of interest or 5' to the DNA segment and in proper reading frame with both the secretory signal sequence and a DNA segment of interest.

The choice of suitable promoters, terminators and secretory signals is well within the level of ordinary skill in the art. Methods for expressing cloned genes in *Saccharomyces cerevisiae* are generally known in the art (see, "Gene Expression Technology," *Methods in Enzymology*, Vol. 185, Goeddel (ed.), Academic Press, San Diego, Calif., 1990 and "Guide to Yeast Genetics and Molecular Biology," *Methods in Enzymology*, Guthrie and Fink (eds.), Academic Press, San Diego, Calif., 1991; which are incorporated herein by reference) . Proteins of the present invention can also be expressed in filamentous fungi, for example, strains of the fungi Aspergillus (McKnight et al., U.S. Pat. No. 4,935,349, which is incorporated herein by reference) . Expression of cloned genes in cultured mammalian cells and in *E. coli*, for example, is discussed in detail in Sambrook et al. (*Molecular Cloning: A Laboratory Manual, Second Edition*, Cold Spring Harbor, N.Y., 1989; which is incorporated herein by reference). As would be evident to one skilled in the art, one could express the proteins of the instant invention in other host cells such as avian, insect and plant cells using regulatory sequences, vectors and methods well established in the literature.

In yeast, suitable yeast vectors for use in the present invention include YRp7 (Struhl et al., *Proc. Natl. Acad. Sci. USA* 76: 1035–1039, 1978), YEp13 (Broach et al., *Gene* 8: 121–133, 1979), POT vectors (Kawasaki et al, U.S. Pat. No. 4,931,373, which is incorporated by reference herein), pJDB249 and pJDB219 (Beggs, *Nature* 275:104–108, 1978) and derivatives thereof. Preferred promoters for use in yeast include promoters from yeast glycolytic genes (Hitzeman et al., *J. Biol. Chem.* 255: 12073–12080, 1980; Alber and Kawasaki, *J. Mol. Appl. Genet.* 1: 419–434, 1982; Kawasaki, U.S. Pat. No. 4,599,311) or alcohol dehydrogenase genes (Young et al., in *Genetic Engineering of Microorganisms for Chemicals*, Hollaender et al., (eds.), p. 355, Plenum, New York, 1982; Ammerer, *Meth. Enzymol.* 101: 192–201, 1983). In this regard, particularly preferred promoters are the TPI1 promoter (Kawasaki, U.S. Pat. No. 4,599,311, 1986) and the ADH2-4$^c$ promoter (Russell et al., *Nature* 304: 652–654, 1983; Irani and Kilgore, U.S. patent application Ser. No. 07/784,653, CA 1,304,020 and EP 284 044, which are incorporated herein by reference). The expression units may also include a transcriptional terminator. A preferred transcriptional terminator is the TPI1 terminator (Alber and Kawasaki, ibid.).

Host cells containing DNA constructs of the present invention are then cultured to produce amyloid protein precursor homologues or Kunitz-type inhibitors. The cells are cultured according to standard methods in a culture medium containing nutrients required for growth of the particular host cells. A variety of suitable media are known in the art and generally include a carbon source, a nitrogen source, essential amino acids, vitamins, minerals and growth factors. The growth medium will generally select for cells containing the DNA construct by, for example, drug selection, complementation of glycolytic gene defect or complementation of a deficiency in an essential nutrient by a selectable marker on the DNA construct or co-transfected with the DNA construct.

Yeast cells, for example, are preferably cultured in a chemically defined medium, comprising a non-amino acid nitrogen source, inorganic salts, vitamins and essential amino acid supplements. The pH of the medium is preferably maintained at a pH greater than 2 and less than 8, preferably at pH 6.5. Methods for maintaining a stable pH include buffering and constant pH control, preferably through the addition of sodium hydroxide. Preferred buffering agents include succinic acid and Bis-Tris (Sigma Chemical Co., St. Louis, Mo.). Yeast cells having a defect in a gene required for asparagine-linked glycosylation are preferably grown in a medium containing an osmotic stabilizer. A preferred osmotic stabilizer is sorbitol supplemented into the medium at a concentration between 0.1M and 1.5M, preferably at 0.5M or 1.0M. Cultured mammalian cells are generally cultured in commercially available serum-containing or serum-free media. Selection of a medium appropriate for the particular host cell used is within the level of ordinary skill in the art.

Within one embodiment of the invention, the proteins of the present invention are expressed in mammalian cells. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Viroloqy* 52:456, 1973), electroporation (Neumann et al., *EMBO J.* 1:841–845, 1982) and DEAE-dextran mediated transfection (Ausubel et al., eds., *Current Protocols in Molecular Biology*, John Wiley and Sons, Inc., N.Y., 1987), which are incorporated herein by reference. The production of recombinant proteins in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314) and 293 (ATCC No. CRL 1573; Graham et al., *J. Gen. Virol.* 36:59–72, 1977) cell lines. Additional suitable cell lines are known in the art and available from public depositories such as the American Type Culture Collection, Rockville, Md.

The recombinant amyloid protein precursor homologues or Kunitz-type inhibitors expressed using the methods described herein are isolated and purified by conventional procedures, including separating the cells from the medium by centrifugation or filtration, precipitating the proteinaceous components of the supernatant or filtrate by means of a salt, e.g. ammonium sulfate, purification by a variety of chromatographic procedures, e.g. ion exchange chromatography or affinity chromatography, or the like. Methods of protein purification are known in the art (see generally, Scopes, R., *Protein Purification*, Springer-Verlag, N.Y. (1982), which is incorporated herein by reference) and may be applied to the purification of the recombinant proteins of the present invention.

Preferably, the Kunitz-type inhibitors of the present invention are purified using the method essentially described by Norris et al. (*Biol. Chem. Hoppe-Seyler* 371: 37–42, 1990, which is incorporated by reference herein in its entirety). Briefly, selected yeast transformants are grown in 10 liters of YEPD for approximately 40 hours at 30° C. until an $OD_{600}$ of approximately 25 has been reached. The culture is centrifuged, and the supernatant is decanted. A 300 ml-1000 ml aliquot of supernatant is adjusted to pH 2.3 and applied to a column holding 8 ml of S-Sepharaose (Pharmacia-LKB Biotechnology AS, Alleroed, Denmark) or the like that has been previously equilibrated with 20 mM Bicine, pH 8.7 (Sigma Chemical Co., St. Louis, Mo.). After the column has been extensively washed with 20 mM Bicine, pH 8.7, the Kunitz-type inhibitor is eluted with 30 ml of 20 mM Bicine, pH 8.7 containing 1M NaCl. The eluted material is desalted by application to a Sephadex G-25 column (a beaded dextran matrix, Pharmacia-LKB Biotechnology AS, Alleroed, Denmark; 2.5×30 cm) or the like that has been equilibrated with 20 mM $NH_4HCO_3$, pH 7.8. The Kunitz-type inhibitor is eluted with 20 mM $NH_4HCO_3$, pH 7.8.

The Kunitz-type inhibitor is further purified and concentrated by chromatography on a Mono S column (Pharmacia-LKB Biotechnology AS, Alleroed, Denmark; 0.5×5 cm) or the like equilibrated with 20 mM Bicine, pH 8.7. After washing with the equilibration buffer at 2 ml/min for 10 minutes, gradient elution of the Kunitz-type inhibitor is carried out over twelve minutes at 1 ml/min from 0–0.6M NaCl in the equilibration buffer. Peak samples are pooled, and the Kunitz-type inhibitor is purified using reverse phase HPLC on a Vydac 214TP510 column (Mikro-lab, Aarhus, Denmark; 1.0×25 cm) or the like with a gradient elution at 4 ml/min from 5% A (0.1% trifluoroacetic acid (TFA) in water) to 45% B (0.7% TFA in acetonitrile) in 20 minutes. The purified product in lyophilized in water, and inhibitor activity is measured.

The present invention also relates to a pharmaceutical composition comprising a Kunitz-type inhibitor of the present invention together with a pharmaceutically acceptable carrier or vehicle. In the composition of the invention, the Kunitz-type inhibitor may be formulated by any of the established methods of formulating pharmaceutical compositions, e.g. as described in *Remington's Pharmaceutical Sciences*, 1985. The composition may typically be in a form suited for systemic injection or infusion and may, as such, be formulated with sterile water or an isotonic saline or glucose solution.

Kunitz-type inhibitors of the present invention are therefore contemplated to be advantageous to use for the therapeutic applications suggested for native aprotinin or aprotinin analogs with other inhibitor profiles, in particular those which necessitate the use of large aprotinin doses. Therapeutic applications for which the use of the Kunitz-type inhibitor of the invention is indicated as a result of its ability to inhibit human serine proteases, e.g. trypsin, plasmin, kallikrein, elastase, cathepsin G and proteinase-3, include (but are not limited to) acute pancreatitis, inflammation, thrombocytopenia, preservation of platelet function, organ preservation, wound healing, shock (and conditions involving hyperfibrinolytic hemorrhage, emphysema, rheumatoid arthritis, adult respiratory distress syndrome, chronic inflammatory bowel disease and psoriasis, in other words diseases presumed to be caused by pathological proteolysis by elastase, cathepsin G and proteinase-3 released from triggered PMNs.

Furthermore, the present invention relates to the use of the Kunitz-type inhibitors as described above for the preparation of a medicament for the prevention or therapy of diseases or conditions associated with pathological proteolysis by proteases released from overstimulated PMNs. As indicated above, it may be an advantage to administer heparin concurrently with the Kunitz-type inhibitors of the present invention.

Apart from the pharmaceutical use indicated above, the Kunitz-type inhibitors as specified above may be used to isolate useful natural substances, e.g. proteases or receptors from human material, which bind directly or indirectly to the Kunitz-type inhibitor, for instance by screening assays or by affinity chromatography.

Within one aspect of the present invention, amyloid protein precursor homologues and Kunitz-type inhibitors, including derivatives thereof, as well as portions or fragments of these proteins, are utilized to prepare antibodies which specifically bind to the amyloid protein precursor homologues and Kunitz-type inhibitors. As used herein, the term "antibodies" includes polyclonal antibodies, monoclonal antibodies, antigen-binding fragments thereof such as F(ab')$_2$ and Fab fragments, as well as recombinantly produced binding partners. These binding partners incorporate the variable regions from a gene which encodes a specifically binding monoclonal antibody. Antibodies are defined to be specifically binding if they bind to the amyloid protein precursor homologue or Kunitz-type inhibitor with a $K_a$ of greater than or equal to $10^7$/M. The affinity of a monoclonal antibody or binding partner may be readily determined by one of ordinary skill in the art (see, Scatchard, *Ann. N.Y. Acad. Sci.* 51: 660–672, 1949).

Methods for preparing polyclonal and monoclonal antibodies have been well described in the literature (see for example, Sambrook et al., ibid.; Hurrell, J. G. R., Ed., *Monoclonal Hybridoma Antibodies: Techniques and Applications*, CRE Press, Inc., Boca Raton, Fla., 1982). As would be evident to one of ordinary skill in the art, polyclonal antibodies may be generated from a variety of warm-blooded animals such as horses, cows, goats, sheep, dogs, chickens, rabbits, mice, or rats. The immunogenicity of an amyloid protein precursor homologue or Kunitz-type inhibitor may be increased through the use of an adjuvant such Freund's complete or incomplete adjuvant. A variety of assays known to those skilled in the art may be utilized to detect antibodies which specifically bind to an amyloid protein precursor homologue or Kunitz-type inhibitor. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radio-immunoassays, radio-immunoprecipitations, enzyme-linked immuno-sorbent assays, dot blot assays, inhibition or competition assays, and sandwich-assays.

Additional techniques for the preparation of monoclonal antibodies may utilized to construct and express recombinant monoclonal antibodies. Briefly, mRNA is isolated from a B cell population and utilized to create heavy and light chain immunoglobulin cDNA expression libraries in a suitable vector such as the λIMMUNOZAP(H) and λIMMUNOZAP(L) vectors, which may be obtained from Stratocyte (La Jolla, Calif.). These vectors are then screened individually or are co-expressed to form Fab fragments or antibodies (Huse et al., *Science* 246: 1275–1281, 1989; Sastry et al., *Proc. Natl. Acad. Sci. USA* 86: 5728–5732, 1989). Positive plaques are subsequently converted to a non-lytic plasmid which allows high level expression of monoclonal antibody fragments in *E. coli*.

Binding partners such as those described above may also be constructed utilizing recombinant DNA techniques to incorporate the variable regions of a gene which encodes a specifically binding antibody. The construction of these proteins may be readily accomplished by one of ordinary skill in the art (see for example, Larrick et al., *Biotechnology* 7: 934–938, 1989; Reichmann et al., *Nature* 322: 323–327, 1988 and Roberts et al. *Nature* 328: 731–734, 1987). Once suitable antibodies or binding partners have been obtained, they may be isolated or purified by many techniques well described in the literature (see for example, *Antibodies: A Laboratory Manual*, ibid.). Suitable techniques include protein or peptide affinity columns, HPLC or RP-HPLC, purification on protein A or protein G columns or any combination of these techniques. Within the context of the present invention, the term "isolated" as used to define antibodies or binding partners means "substantially free of other blood components."

Antibodies and binding partners of the present invention may be used in a variety of ways. The tissue distribution of amyloid protein precursor homologues, for example, may be determined by incubating tissue slices with a labeled monoclonal antibody which specifically binds to the amyloid protein precursor homologue, followed by detection of the presence of the bound antibody. Labels suitable for use within the present invention are well known in the art and include, among others, fluorescein, isothiocyanate, phycoerythrin, horseradish peroxidase, and colloidal gold.

The antibodies of the present invention may also be used for the purification of amyloid protein precursor homologues and Kunitz-type inhibitors of the present invention. The coupling of antibodies to solid supports and their use in purification of proteins is well known in the literature (see for example, *Methods in Molecular Biology*, Vol. 1, Walker (Ed.), Humana Press, New Jersey, 1984, which is incorporated by reference herein in its entirety).

The following examples are offered by way of illustration, not by way of limitation.

EXAMPLES

Restriction endonucleases and other DNA modification enzymes (e.g., T4 polynucleotide kinase, calf alkaline phosphatase, DNA polymerase I (Klenow fragment), T4 polynucleotide ligase) were obtained from GIBCO BRL Life Technologies, Inc (GIBCO BRL) and New England Biolabs and were used as directed by the manufacturer, unless otherwise noted.

Oligonucleotides were synthesized on an Applied Biosystems Model 380A DNA synthesizer and purified by polyacrylamide gel electrophoresis on denaturing gels. *E. coli* cells were transformed as described by Maniatis et al. (*Molecular Cloning: A Laboratory Manual*, Cold Spring Harbor Laboratory, 1982) or Sambrook et al. (*Molecular Cloning: A Laboratory Manual*, 2 ed., Cold Spring Harbor, N.Y., 1989). Radiolabeled probes and hybridization solutions were prepared essentially as described by Sambrook et al. (*Molecular Cloning: A Laboratory Manual*, 2 ed., Cold Spring Harbor, N.Y., 1989; which is incorporated by reference herein in its entirety).

Example 1
Cloning of An Amyloid Precursor Protein cDNA

Poly(A)$^+$ RNAs from a variety of human tissue sources were screened using an antisense 30-mer oligonucleotide (ZC4792; SEQ ID NO:5). A blot of human poly(A)$^+$ RNA from heart, brain, placenta, liver, lung, skeletal muscle, kidney and pancreas (HUMAN MTN BLOT) was obtained from Clontech Laboratories, Inc. (Palo Alto, Calif.). The blot was prehybridized in a prehybridization solution containing 5× SSPE (Table 1), 2× Denhardt's (Table 1), 0.5% sodium dodecyl sulfate (SDS), and 100 μg/ml sonicated salmon sperm DNA for four hours at 55° C. After prehybridization, the prehybridization solution was removed and replaced with prehybridization solution containing 4.7×10$^6$ cpm/ml of $^{32}$P-labeled ZC4792 (SEQ ID NO:5). After an overnight incubation at 55° C. the hybridization solution was removed, and the blot was washed once in 2× SSC (Table 1), 0.05% SDS at room temperature for 20 minutes followed by a wash in 2× SSC (Table 1), 0.1% SDS for 20 minutes at 55° C. The blot was exposed to film for two and a half hours. The resulting autoradiograph showed a number of bands in most of the lanes, indicating the presence of related sequences in most of the tissues represented in the blot. The blot was washed at a higher stringency in 2× SSC (Table 1) at 60–65° C. for 30 minutes, after which the blot was exposed to film overnight. The second autoradiograph showed the presence of a 1.6 kb band for placenta and liver and an apparently smaller band of approximately 1.2 kb in the pancreas.

TABLE 1
20× SSPE
- 175.3 g NaCl
- 27.6 g NaH$_2$PO4.H$_2$O
- 7.4 g EDTA

Dissolve the solids in 800 ml of distilled water. Adjust the pH to 7.4 with NaOH (approximately 6.5 ml of a 10N solution). Adjust the volume to 1 liter with distilled water. Sterilize by autoclaving.

50× Denhardt's
- 5 g Ficoll
- 5 g polyvinylpyrrolidone
- 5 g bovine serum albumin (Fraction V)

Dissolve the solids into a final volume of 500 ml. Filter the solution to sterilize and store at −20° C.

20× SSC
- 175.3 g NaCl
- 88.2 g sodium citrate

Dissolve the solids in 800 ml of distilled water. Adjust the pH to 7.0 by a drop-wise addition of 10N NaOH. Adjust the volume to 1 liter with distilled water. Sterilize by autoclaving.

Prehybridization Solution #1
- 5× SSPE
- 5× Denhardt's
- 0.5% SDS
- 100 μg/ml sheared salmon sperm DNA Prehybridization Solution #2
- 5× SSC
- 5× Denhardt's
- 0.1% SDS
- 100 μg/ml sheared salmon sperm DNA Growth Medium
- Dulbecco's Modified Eagle's Medium (DMEM) containing 5% fetal bovine serum, 2 mM L-glutamate, 1× PSN (50 μg/ml penicillin, 50 μg/ml streptomycin, 100 μg/ml neomycin; GIBCO BRL), 10 μM methotrexate.

Serum-free Medium
- 500 ml Dulbecco's Modified Eagle's Medium (DMEM)
- 0.29 mg/ml L-glutamine
- 10 mg/l transferrin
- 5 mg/l fetuin (Aldrich, Milwaukee, Wis.)
- 5 mg/l insulin (GIBCO BRL, Grand Island, N.Y.)
- 2 μg/l selenium (Aldrich, Milwaukee, Wis.)
- In addition to the above ingredients, the medium was supplemented with 10 μM methotrexate, 25–50 mM HEPES BUFFER SOLUTION (N-2-Hydroxyethylpiperazine-N'-2-Ethane Sulfonic Acid (pH 7.2); JRH Biosciences, Lenxa, Kans.) and 1× PSN (GIBCO BRL).

Phosphate Buffered Saline (PBS)
- 8 g sodium chloride
- 0.2 g potassium chloride
- 1 g sodium phosphate
- 2 g potassium phosphate Dissolve solids in distilled water. Bring volume to 1 liter. Autoclave to sterilize.

To obtain a cDNA sequence encoding a protease inhibitor from the Kunitz family from human placenta, a human placenta cDNA library in λgt11 was screened using the radio-labeled ZC4792 (SEQ ID NO:5). Poly(A)$^+$ RNA obtained from human placenta was used to prepare a λgt11 cDNA library essentially as described by Hagen et al. (*Proc. Natl. Acad. Sci. USA* 83: 2412–2416, 1986 and U.S. Pat. No. 4,784,950, which are incorporated herein by reference in their entirety). The library was titered, and 50,000 pfu/plate were plated on a total of twenty plates to obtain one million independent plaques. Duplicate plaque lifts were prepared using ICN BIOTRANS nylon membranes (ICN, Irvine, Calif.). The membranes were prewashed in 5× SSC (Table 1), 0.5% SDS at 50° C. for one hour followed by an overnight prehybridization at 55° C. in prehybridization solution #1 (Table 1). The prehybridization solution was removed and replaced with fresh prehybridization solution #1 containing $1.6 \times 10^8$ cpm of ZC4792 probe (SEQ ID NO:5). Hybridization was carried out under the same conditions as the prehybridization. After hybridization, the solution was removed, and the blots were washed at 60° C. in 2× SSC (Table 1), 0.1% SDS. Eleven positive plaques were identified and plaque purified.

Phage DNA prepared from each purified phage clone was digested with Eco RI to isolate the cDNA insert. The Eco RI fragments, which ranged in size from 2.0–3.5 kb, were then subcloned into Eco RI-linearized PUC19. Sequence analysis of the cloned fragments demonstrated that the clones showed some homology to the Kunitz family of protease inhibitors. Selected clones were subjected to extensive sequence analysis and were shown to have strong homology to human amyloid protein precursor homologue (Ponte et al., ibid.), which contains a Kunitz-type inhibitor domain. Two clones, ZGKI13 and ZGKI20, which encoded approximately 3.5 kb and approximately 2.5 kb cDNA inserts, respectively, were selected for further analysis. Plasmids ZGKI13 and ZGKI20 were deposited on Oct. 14, 1992 with the American Type Culture Collection (12301 Parklawn Dr., Rockville, Md.) under accession numbers 69090 and 69089, respectively. Plasmids ZGKI13 and ZGKI20 were shown to contain the identical partial sequence shown in SEQ ID NOS: 1 and 2.

A comparison of the sequences of clones ZGKI13, ZGKI20 and one other positive clones showed that clone ZGKI13 contained a mutation at amino acid codon 160 (from the initiation methionine) which resulted in a Trp codon instead of a Cys codon. Clone ZGKI20 contained the correct Cys codon at 160. A corrected CDNA constructed using the cDNAs in clones ZGKI13 and ZGKI20 was corrected and subcloned into plasmid Zem229R. Plasmid Zem229R is a mammalian expression vector modified from Zem229, which is a pUC18-based expression vector containing a unique Bam HI site for insertion of cloned DNA between the mouse metallothionein-1 promoter and SV40 transcription terminator and an expression unit containing the SV40 early promoter, mouse dihydrofolate reductase gene, and SV40 terminator. Plasmid Zem229R was deposited as an *E. coli* transformant with the American Type Culture Collection (12301 Park Lawn Drive, Rockville Md.) on Sep. 28, 1993 under accession number 69447. Plasmid Zem229 was modified to delete the two Eco RI sites by partial digestion with Eco RI, blunting with DNA polymerase I (Klenow fragment) and dNTPs, and religation. Digestion of the resulting plasmid with Bam HI followed by ligation of the linearized plasmid with Bam HI-Eco RI adapters resulted in a unique Eco RI cloning site. The resulting plasmid was designated Zem229R. A plasmid containing the corrected sequence was designated APPH. Clone ZGKI20 was digested with Nsi I and Bgl II to obtain the 547 bp fragment containing the correct sequence. Clone ZGKI13 was digested with Eco RI and Nsi I and with Bgl II and Eco RI to isolate the 266 bp Eco RI-Nsi I and the 2934 bp Bgl II-Eco RI fragments, respectively. The three fragments were ligated in a four-part ligation with Eco RI-linearized Zem229R. A plasmid containing the corrected CDNA in the correct orientation relative to the metallothionein-1 promoter, designated APPH, was deposited with the American Type Culture Collection (12301 ParkLawn Drive, Rockville, Md.) on Sep. 17, 1993 under accession number 69424 as an *E. coli* transformant. The APPH coding sequence and deduced amino acid sequence are shown in SEQ ID NO:12 and SEQ ID NO:13.

Example 2

Expression of Kunitz-Type Inhibitor Domains

A. Expression of a Kunitz-type Inhibitor Domain of the Amyloid Precursor Protein Homoloque Comprising Amino Acids 56 through 110 of SEQ ID NO:2

The Kunitz-type inhibitor domain encoded in plasmid ZGKI20 and comprising the amino acid sequence of SEQ ID NO:2 from alanine, amino acid 56 through alanine, amino acid number 110 was expressed in a strain of the yeast *Saccharomyces cerevisiae* from a PCR-generated sequence. The DNA sequence encoding the Kunitz-type inhibitor domain was amplified from human genomic DNA obtained from Clontech Laboratories, Inc. (Palo Alto, Calif.). Synthetic oligonucleotide primers M-1252 and M-1251 (SEQ ID NOS:7 and 6, respectively) were designed as PCR amplification primers. Synthetic oligonucleotide M-1252 is complementary to nucleotides 313–332 of SEQ ID NO:1, and in addition carries a 5' extension containing a translation stop codon followed by an Xba I site. Oligonucleotide M-1251 contains a sequence that is identical to nucleotides 215–235 of the synthetic leader sequence shown in SEQ ID NO:3 followed by nucleotides 168–187 of SEQ ID NO:1. A PCR reaction was performed in a 100 μl final volume using 1 μg of human genomic DNA (Clontech Laboratories, Inc.), 100 pmole each of oligonucleotides M-1251 and M-1252 (SEQ ID NOS:6 and 7, respectively), and the reagents provided in the GENEAMP kit (Perkin Elmer Cetus, Norwalk, Conn.) according to the manufacturer's instructions. The reaction was amplified for nineteen cycles (20 seconds at 94° C., 20 seconds at 50° C., and 30 seconds at 72° C.) followed by a ten minute incubation at 72° C. A 201 bp fragment was isolated by agarose gel electrophoresis.

A DNA sequence encoding the synthetic signal sequence (SEQ ID NO:3) was obtained by PCR amplification of a fragment from plasmid pKFN-1000. Plasmid pKFN-1000 is a derivative of plasmid pTZ19R (Mead et al., *Prot. Engin.* 1: 67–74, 1986) containing a DNA sequence encoding a synthetic yeast signal leader peptide. Plasmid pKFN-1000 is described in WO 90/10075, which is incorporated by reference herein in its entirety. The DNA sequence of the 235 base pairs downstream from the Eco RI site of plasmid pKFN-1000 and the encoded amino acid sequence is shown in SEQ ID NOS:3 and 4. A 0.7 kb Pvu II fragment of plasmid pKFN-1000 was used as a template. Synthetic oligonucleotide NOR-1478 (SEQ ID NO:8) is identical to a sequence just upstream of the Eco RI site (nucleotides to 1–6 of SEQ ID NO:3). Synthetic oligonucleotide NOR-2523 (SEQ ID NO:9) is complementary to nucleotides 215–235 of the coding sequence in SEQ ID NO:3. A PCR reaction was performed in a 100 μl final volume using 0.1 μg of the 0.7 kb Pvu II fragment, 100 pmoles each of oligonucleotide NOR-1478 and NOR-2523 (SEQ ID NOS:8 and 9, respectively) and reagents from the GENEAMP commercial kit (Perkin Elmer Cetus) according to the manufacturer's instructions. The PCR reaction was amplified as described above. A 257 bp PCR product was isolated by agarose gel electrophoresis.

A DNA sequence encoding the complete synthetic signal sequence operatively linked to the Kunitz-type inhibitor domain sequence was obtained by amplifying the two PCR fragments described above. A PCR reaction was performed as described above using 100 pmoles each of primers NOR-1478 (SEQ ID NO:8) and M-1252 (SEQ ID NO:7) and 0.1 μg of each of the two PCR fragments described above. The PCR reaction was amplified for sixteen cycles (1 minute at 94° C., 2 minutes at 50° C., 3 minutes at 71° C.) followed by a ten minute incubation at 72° C. A 437 bp fragment was purified by agarose gel electrophoresis. The fragment was then digested with Eco RI and Xba I, and the resulting 404 bp fragment was ligated with plasmid pTZ19R, which had been linearized by digestion with Eco RI and Xba I. The ligation mixture was transformed into competent restriction minus, modification plus E. coli strain, and transformants were selected in the presence of ampicillin. Plasmid DNAs prepared from selected transformants were sequenced, and a plasmid containing the DNA sequence of the synthetic yeast signal sequence fused to the Kunitz-type inhibitor domain was identified.

The Eco RI-Xba I fragment encoding the secretory signal-Kunitz-type inhibitor domain was then isolated and subcloned into plasmid pMT-636. Plasmid pMT-636 is derived from the shuttle vector PCPOT (Plasmid pCPOT was deposited on May 9, 1984 with the American Type Culture Collection; 12301 Parklawn Dr., Rockville, Md.; under Accession No. 39685) in which the 0.4 kb Hpa I-Nru I fragment containing the *Saccharomyces cerevisiae* LEU2 gene was deleted and, in addition, contains the *Saccharomyces cerevisiae* TPI1 promoter and the TPI1 terminator flanking an Eco RI-Xba I directional cloning site such that the a DNA insert is transcribed in the same direction as the *Schizosaccharomyces pombe* POT1 gene (Norris et al., ibid.). Plasmid pMT-636 has been described in WO 89/01968 and WO 90/10075, which are incorporated herein by reference in their entirety. Plasmid pMT-636 was digested with Nco I and Xba I to isolate the 9.3 kb fragment. Plasmid pMT-636 was also digested with Nco I and Eco RI to obtaion the 1.6 kb fragment. The two fragments from pMT-636 were ligated with the Eco RI-Xba I fragment.

A plasmid containing the signal sequence-Kunitz-:-type inhibitor domain fragment in the correct orientation was transformed into *S. cerevisiae* MT-663 (a/α Δtpi/Δtpi pep4-3/pen4-3). Transformants were selected for growth on glucose as the sole carbon source, and cultivated in YEPD media. Transformants were assayed for activity as described in Example 3. The Kunitz-type inhibitor is purified as described in Example 4.

B. Expression of a Kunitz-type Inhibitor Domain of the Amyloid Precursor Protein Homologue comprising Amino Acids 53 through 110 of SEQ ID NO:2

A DNA construct encoding a Kunitz-type inhibitor domain the Kunitz-type inhibitor domain comprising the amino acid sequence of SEQ ID NO:2 from aspartic acid, amino acid number 53, through alanine, amino acid number 110, was amplified from human genomic DNA as described in Example 1 using oligonucleotide primers M-1252 and M-1249 (SEQ ID NOS:7 and 10). The resulting PCR-generated fragment was gel-purified and joined to the signal sequence as described above. The fragment encoding the signal sequence-Kunitz-type inhibitor was then subcloned into a yeast expression vector and transformed into *Saccharomyces cerevisiae* strain MT-663 as described above.

Selected transformants were assayed for activity as described in Example 3. The Kunitz-type inhibitor is purified as described in Example 4.

C. Expression of a Kunitz-type Inhibitor Domain of the Amyloid Precursor Protein Homologue Comprising A Glutamic Acid Residue Followed by Amino Acids 57 through 110 of SEQ ID NO:2

A DNA construct encoding a Kunitz-type inhibitor comprising the amino acid sequence of SEQ ID NO:2 from valine, amino acid number 57, through alanine, amino acid number 110, and which further contains a glutamic acid immediately N-terminal to valine was amplified from human genomic DNA as described in Example 1 using oligonucleotide primers M-1252 and M-1250 (SEQ ID NOS:7 and 11). The resulting PCR-generated fragment was gel-purified and joined to the signal sequence as described above. The fragment encoding the signal sequence-Kunitz-type inhibitor was then subcloned into a yeast expression vector and transformed into *Saccharomyces cerevisiae* strain MT-663 as described above.

Selected transformants were assayed for activity as described in Example 3. The Kunitz-type inhibitor is purified as described in Example 4.

D. Expression of the Amyloid Precursor Protein Homologue in Mammalian Cells

Plasmid APPH DNA, encoding the amyloid precursor protein homologue was used to transfect BHK570 cells using calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973). BHK 570 cells were deposited with the American Type Culture Collection (ATCC; 12301 Parklawn Dr., Rockville, Md., 20852, USA) on Dec. 20, 1989 under accession number CRL 10314. Transfected cells were initially selected in the presence of medium containing 1 μM of methotrexate followed by more stringent selection in medium containing 10 μM methotrexate. Following selection in 10 μM methotrexate, randomly selected clones were grown to confluency in 6-well dishes in Growth Medium (Table 1). After reaching confluency, the spent medium was decanted, and the cells were washed with PBS (Phosphate Buffered Saline; Table 1) to remove any remaining serum. Serum-free medium (Table 1) was added to the cells, and the cells were grown for 24–48 hours. The conditioned media was collected and assayed for trypsin inhibitor activity using the assay method detailed in Example 4B.

E. Expression of a Kunitz-type Inhibitor domain of the Amyloid Precursor Protein The Kunitz-type inhibitor domain of the amyloid protein precursor (SEQ ID NO:17) was expressed in a strain of the yeast *Saccharomyces cerevisiae* from a PCR-generated sequence. The DNA sequence encoding the Kunitz-type inhibitor domain was amplified from human genomic DNA obtained from Clontech Laboratories, Inc. (Palo Alto, Calif.) essentially as described above. Synthetic oligonucleotide primers primer 1 and primer 2 (SEQ ID NOS:14 and 15, respectively) were designed as PCR amplification primers. Synthetic oligonucleotide primer 2 (SEQ ID NO:15) is complementary to nucleotides 151–168 of SEQ ID NO:16, and in addition carries a 5' extension containing a translation stop codon followed by an Xba I site. Oligonucleotide primer 1 (SEQ ID NO:14) contains a sequence that is identical to nucleotides 215–235 of the synthetic leader sequence shown in SEQ ID NO:3 followed by nucleotides 1–16 of SEQ ID NO:16. A PCR reaction was performed in a 100 μl final volume using 1 μg of human genomic DNA (Clontech Laboratories, Inc.), 100 pmole each of oligonucleotides primer 1 and primer 2 (SEQ ID NOS:14 and 15, respectively), and the reagents provided in the GENEAMP kit (Perkin Elmer Cetus, Norwalk, Conn.) according to the manufacturer's instructions. The reaction was amplified for nineteen cycles (20 seconds at 94° C., 20 seconds at 50° C., and 30 seconds at 72° C.) followed by a ten minute incubation at 72° C. A 201 bp fragment was isolated by agarose gel electrophoresis.

A DNA sequence encoding the synthetic signal sequence (SEQ ID NO:3) was obtained by PCR amplification of a fragment from plasmid pKFN-1000 as described above. A DNA sequence encoding the complete synthetic signal sequence operatively linked to the Kunitz-type inhibitor domain sequence was obtained by amplifying the two PCR fragments described above. A PCR reaction was performed as described above using 100 pmoles each of primers NOR-1478 (SEQ ID NO:8) and primer 2 (SEQ ID NO:15) and 0.1 µg of each of the two PCR fragments described above. The PCR reaction was amplified for sixteen cycles (1 minute at 94° C., 2 minutes at 50° C., 3 minutes at 71° C.) followed by a ten minute incubation at 72° C. A 437 bp fragment was purified by agarose gel electrophoresis. The fragment was then digested with Eco RI and Xba I, and the resulting fragment was ligated with plasmid pTZ19R as described above. The ligation mixture was transformed into competent restriction minus, modification plus *E. coli* strain, and transformants were selected in the presence of ampicillin. Plasmid DNAs prepared from selected transformants were sequenced, and a plasmid containing the DNA sequence of the synthetic yeast signal sequence fused to the APP Kunitz-type inhibitor domain was identified.

The Eco RI-Xba I fragment encoding the secretory signal-Kunitz-type inhibitor domain was then isolated and subcloned into plasmid pMT-636 as described above. A plasmid containing the signal sequence-APP Kunitz-type inhibitor domain fragment in the correct orientation was transformed into *S. cerevisiae* MT-663 (a/αΔkl/Δtpi pep4-3/pep4-3). Transformants were selected for growth on glucose as the sole carbon source, and cultivated in YEPD media. Transformants were assayed for activity as described in Example 3. The amyloid precursor protein Kunitz-type inhibitor was purified as described in Example 4.

Example 3

Activity Assays

A. Trypsin Inhibitory -Activity Assay on Yeast Culture Supernatants

Trypsin inhibitory activity was measured on the spent media from cultures of yeast transformants described in Example 2 by diluting 3.2 µl of each spent medium sample with 80 µl of assay buffer (50 mM Tris HCl, pH 7.4, 100 mM NaCl, 2 mM CaCl$_2$, 0. 1% w/v PEG 20,000). The diluted supernatant was added to 80 µl of 133 nM bovine trypsin (Novo Nordisk A/S) diluted in assay buffer, and the mixture was incubated for 10 minutes at room temperature. After incubation, 100 µl of 1.8 mM peptidyl nitroanilide substrate S2251 (D-Val-Leu-Lys-Nan; Kabi) diluted in assay buffer was added to each sample, and the samples were incubated with the substrate for 30 minutes. Trypsin inhibitory activity, as indicated by a colorless solution, was found in supernatants from the yeast strains described in Example 2. A control reaction, which resulted in a yellow solution, was produced by a supernatant from a yeast strain not expressing any Kunitz-type inhibitor.

B. Trypsin Inhibitory Activity Assay on Mammalian Cell Culture Supernatants

Conditioned media from cells expressing Kunitz-type inhibitors was assayed for trypsin inhibitor activity. For each clone, 20–100 µl of conditioned medium was added to a solution containing 2.4 µg/ml trypsin (Worthington Biochemical, Freehold, N.J.) in 100 mM NaCl, 50 mM Tris (pH 7.4) to give a final volume of 300 µl. The reactions were incubated at 23° C. for 30 minutes after which the chromogenic substrate S-2251 (D-Val-Leu-Lys-Nan; Chromogenix, Franklin, Ohio) to a final concentration of 0.6 mM. The residual trypsin activity was measured by absorbance at 405 nm.

C. Protease Inhibitory Activity Assays

Protease inhibitory profiles of the Kunitz inhibitors were determined for a variety of proteases using the chromogenic substrates listed in Table 2 and compared to the inhibitory activity shown by the Kunitz-type inhibitor domain of the amyloid protein precursor (Example 2E) and bovine aprotinin (amino acids 1–58 as described by Norris et al., ibid.; which is incorporated by reference herein in its entirety).

TABLE 2

| Protease (concentration) Source | Substrate (concentration) Source |
| --- | --- |
| Trypsin (8 nM) Novo Nordisk A/S, Bagsvaerd, Denmark | H-D-Val—Leu—Lys—pNA (0.6 mM) Kabi |
| Chymotrypsin (2.5 nM) Novo Nordisk A/S | MeO—Suc—Arg—Pro—Tyr—pNA (0.6 mM) Kabi |
| GL Kallikrein (1 U/ml) Sigma, St Louis, MO | H-D-Val—Leu—Arg—pNA (0.6 mM) Kabi |
| Plasmin (10 nM) Kabi | H-D-Val—Leu—Lys—pNA (0.6 mM) Kabi |
| Urokinase (5 nM) Serono Freigurg, Germany | <Glu—Gly—Arg—pNA (0.6 mM) Kabi |
| rec. Protein Ca (5 nM) Novo Nordisk A/S | <Glu—Pro—Arg—pNA (0.6 mM) Kabi |
| PL Kallikrein (3 nM) Kabi | H-D-Pro—Phe—Arg—pNA (0.6 mM) Kabi |
| human Factor XIIa (30 nM) Dr. Walt Kisiel University of New Mexico, Albuquerque, NM | H-D-Pro—Phe—Arg—pNA (0.6 mM) Kabi |
| human Factor XIa (1 nM) Dr. Kazuo Fujikawa University of Washington, Seattle, WA | Boc—Glu(OBzl)—Ala—Arg—MCA (0.12 mM) Peptide Institute Osaka, Japan |
| human Factor Xa (3 nM) Dr. I. Schousboe Copenhagen, Denmark | MeO—CO—CHA—Gly—Arg—pNA (0.3 mM) NycoMed Oslo, Norway |
| rec. human Factor VIIa (300 nM) Novo Nordisk A/S | H-D-Ile—Pro—Arg—pNA (0.6 mM) Kabi |
| Leukocyte Elastase purified at Novo Nordisk A/S using the method of Baugh and Travis (Biochemistry 15: 836–843, 1976) | MeO—Suc—Ala—Ala—Pro—Val—pNA (0.6 mM) (SEQ ID NO:18) Sigma Chemical Co. St. Louis, MO |
| Cathepsin G purified at Novo Nordisk A/S using the method of Baugh and Travis (Biochemistry 15: 836—843, 1976) | Suc—Ala—Ala—Pro—Phe—pNA (0.6 mM) (SEQ ID NO:19) Sigma Chemical Co. |

Abbreviations in Table 2:
rec. refers to recombinant, GL kallikrein refers to glandular kallikrein, and PL kallikrein refers to plasma kallikrein.

Inhibition assays were performed in microtiter wells in a total volume of 300 µl in 10 mM NaCl, 50 mM Tris-HCl (pH 7.4), 0.01% TWEEN80 (Polyoxyethylenesorbitan monoleate). Each reaction contained 1 µM of the sample inhibitor and one of the proteases at the concentration listed in Table 2. The reactions were incubated at 25° C. for ten minutes after which the appropriate chromogenic substrate was added to the final concentration listed in Table 2 and the final reaction was incubated for thirty minutes at 25° C. Amidolytic activity was measured at 405 nm or by fluorescence Em at 460 nm. Percent inhibition was determined relative to reactions carried out in the absence of inhibitor representing 100% activity or 0% inhibition. The results of the assay are shown in Table 3.

TABLE 3

| | % Inhibition | | |
|---|---|---|---|
| Protease | APPH | APP | BPTI |
| Trypsin | 99.6 | 99.7 | 100 |
| Chymotrypsin | 61 | 94 | 91.3 |
| Gl Kallikrein | 97 | 82 | 91.4 |
| Plasmin | 77 | 90 | 100 |
| Urokinase | 2 | 0 | 1 |
| r. h. Protein Ca | 0 | 1 | 38 |
| PL kallikrein | 69 | 71 | 83 |
| h. FactorXlla | 6 | 8 | 2 |
| h. Factor XIa | 99.8 | 100 | 59 |
| h. Factor Xa | 0 | 29 | 1 |
| r. h. Factor VIIa | 15 | 7 | 1 |
| Leukocyte Elastase | 4 | 6 | 1 |
| Cathepsin G | 0 | 16 | 4 |

The abbreviations in Table 3:
r.h. refers to recombinant human, h. refers to human, protein Ca refers to activated protein C; APPH refers to the Kunitz-Type inhibitor domain of Example 2E, APP refers to the amyloid protein precursor Kunitz-Type inhibitor domain (Example 2E) and BPTI refers to bovine aprotinin (amino acids 1–58).

Example 4
Purification of Kunitz-Type Inhibitors

Kunitz-type inhibitors are purified essentially as described by Norris et al. (ibid.; which is incorporated herein by reference). Selected transformants are grown in 10 liters of YEPD for approximately four days at 30° C. until an $OD_{600}$ of approximately 30 had been reached. At the end of the fermentation, the pH of the culture was adjusted to 3.0 by the addition of concentrated $H_3PO_4$. The culture was centrifuged, and the supernatant was decanted.

For purification, approximately 1 liter of supernatant was adjusted to pH 8.0 by the addition of solid Tris-HCl to a final concentration of 50 mM and titration with 4M NaOH. The supernatant was filtered before it was applied to a column of bovine trypsin that adsorbed to CNBr-activated Sepharose (350 mg bovine trypsin per 35 ml gel). The column was washed with 150 ml 0.1 Tris-HCl (pH 8.0), 0.5M NaCl followed by 150 ml 0.01M Tris-HCl (pH 8.0). After the 0.01M Tris-HCl (pH 8.0) wash, the bound material was eluted with 200 ml 0.2M glycine-HCl (pH 3.0). Fractions of 10 ml each were collected and were analyzed by reverse phase HPLC. Protein-containing fractions were then pooled.

The pooled material was applied to a preparative reverse phase HPLC column (Vydac, The Separations Group, Hesperia, Calif. or the like) that had been equilibrated with 5% B (0.7% TFA in acetonitrile) and 95% A (0.1% TFA in $H_2O$). The flow rate across the column was maintained at 4 ml/min. Following sample application, the column was washed with 5% B until a baseline at 214 nm was achieved. Gradient elution with fraction collection was performed from 5 to 85% B over 80 min. Fractions containing UV-absorbing material were analyzed by reverse phase HPLC (Vydac) and were combined to give pools of chromatographically pure material. Solvent was removed from the pooled fractions by vacuum centrifugation. The concentration and total yield of inhibitor in the major pools was estimated by reverse phase HPLC analysis and by comparison to a bovine aprotinin standard. The final preparations were characterized by electrospray mass spectroscopy (SCIEX API III or the likeu).

Kunitz inhibitor activity is measured using the method essentially described by Norris et al. (ibid.). Briefly, various fixed concentrations of the Kunitz-type inhibitor are incubated in the presence of 0.24 µg/ml of porcine trypsin (Novo Nordisk A/S, Bagsvaerd, Denmark), 12.8 CU/l human plasmin (Kabi, Stockholm, Sweden) or 0.16 nkat/ml human plasma kallikrein (Kabi) in 100 mM NaCl, 50 mM Tris HCl, pH 7.4. After a 30 minute incubation the residual enzymatic activity is measured by the degradation of a solution containing 0.6 mM of either of the chromogenic peptidyl nitroanilide trypsin/plasmin substrates S2251 (D-Val-Leu-Lys-Nan; Kabi) or S2302 (D-Pro-Phe-Arg-Nan; Kabi) in assay buffer. The samples are incubated for 30 minutes after which the absorbance of each sample is measured at 405 nm. Plasmin or trypsin activity is measured as a decrease in absorbance at 405 nm. From the results, the apparent inhibition constant Ki is calculated.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated monoclonal antibody which specifically binds to a human amyloid protein precursor homologue consisting of the amino acid sequence of SEQ ID NO: 13 from methionine, amino acid number 1, to isoleucine, amino acid number 763.

2. A hybridoma which produces the monoclonal antibody of claim 1.

3. An isolated monoclonal antibody which specifically binds to a human Kunitz-type inhibitor consisting of the amino acid sequence of SEQ ID NO:2 from alanine, amino acid number 56 to alanine, amino acid number 110; the amino acid sequence of SEQ ID NO:2 from aspartic acid, amino acid number 53 to alanine, amino acid number 110; or the amino acid sequence of SEQ ID NO:2 from valine, amino acid number 57 to alanine, amino acid number 110 and which further contains a glutamic acid residue on the amino terminus.

4. A hybridoma which produces the monoclonal antibody of claim 3.

5. A method of producing an antibody comprising:
inoculating a warm-blooded animal with a polypeptide immunogen from the group consisting of:
(a) a human amyloid protein precursor homolog polypeptide of an amino acid sequence as shown in SEQ ID NO:13, from methionine, amino acid number 1, to isoleucine, amino acid number 763;
(b) a human Kunitz-type inhibitor polypeptide with an amino acid sequence as shown in SEQ ID NO:2 from alanine, amino acid number 56 to alanine, amino acid number 110;
(c) a human Kunitz-type inhibitor polypeptide with an amino acid sequence as shown in SEQ ID NO:2 from aspartic acid, amino acid number 53 to alanine, amino acid number 110; and
(d) a human Kunitz-type inhibitor polypeptide with an amino acid sequence as shown in SEQ ID NO:2 from valine, amino acid number 57 to alanine, amino acid number 110 and which further contains a glutamic acid residue on the amino terminus, wherein antibodies are generated in the animal; and isolating the antibody from the animal.

6. An isolated monoclonal antibody produced by the method of claim 5 which specifically binds to a human amyloid protein precursor homologue consisting of the amino acid sequence of SEQ ID NO:13 from methionine, amino acid number 1, to isoleucine, amino acid number 763.

7. An isolated monoclonal antibody produced by the method of claim 5 which specifically binds to a human Kunitz-type inhibitor consisting of the amino acid sequence of SEQ ID NO:2 from alanine, amino acid number 56 to alanine, amino acid number 110; the amino acid sequence of SEQ ID NO:2 from aspartic acid, amino acid number 53 to alanine, amino acid number 110; or the amino acid sequence of SEQ ID NO:2 from valine, amino acid number 57 to alanine, amino acid number 110 and which further contains a glutamic acid residue on the amino terminus.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 399 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (B) CLONE: ZGKI13 and ZGKI20

(ix) FEATURE:
      (A) NAME/KEY: CDS
      (B) LOCATION: 3..398

(xi) SEQUENCE DESCRIPTION: SEQ ID NO:1:

| | | |
|---|---|---|
| CA GCT GTG GAT GAG GAT GAT GAG GAT GAG GAA GAA GGG GAG GAA GTG<br>   Ala Val Asp Glu Asp Asp Glu Asp Glu Glu Glu Gly Glu Glu Val<br>    1             5                     10                15 | 47 |
| GTG GAG GAC CGA GAT TAC TAC TAT GAC ACC TTC AAA GGA GAT GAC TAC<br>Val Glu Asp Arg Asp Tyr Tyr Tyr Asp Thr Phe Lys Gly Asp Asp Tyr<br>               20                   25               30 | 95 |
| AAT GAG GAG AAT CCT ACT GAA CCC GGC AGC GAC GGC ACC ATG TCA GAC<br>Asn Glu Glu Asn Pro Thr Glu Pro Gly Ser Asp Gly Thr Met Ser Asp<br>         35                    40                 45 | 143 |
| AAG GAA ATT ACT CAT GAT GTC AAA GCT GTC TGC TCC CAG GAG GCG ATG<br>Lys Glu Ile Thr His Asp Val Lys Ala Val Cys Ser Gln Glu Ala Met<br>            50                 55                60 | 191 |
| ACG GGG CCC TGC CGG GCC GTG ATG CCT CGT TGG TAC TTC GAC CTC TCC<br>Thr Gly Pro Cys Arg Ala Val Met Pro Arg Trp Tyr Phe Asp Leu Ser<br>  65               70                   75 | 239 |
| AAG GGA AAG TGC GTG CGC TTT ATA TAT GGT GGC TGC GGC GGC AAC AGG<br>Lys Gly Lys Cys Val Arg Phe Ile Tyr Gly Gly Cys Gly Gly Asn Arg<br> 80               85                   90               95 | 287 |
| AAC AAT TTT GAG TCT GAG GAT TAT TGT ATG GCT GTG TGT AAA GCG ATG<br>Asn Asn Phe Glu Ser Glu Asp Tyr Cys Met Ala Val Cys Lys Ala Met<br>               100               105             110 | 335 |
| ATT CCT CCA ACT CCT CTG CCA ACC AAT GAT GTT GAT GTG TAT TTC GAG<br>Ile Pro Pro Thr Pro Leu Pro Thr Asn Asp Val Asp Val Tyr Phe Glu<br>         115                   120              125 | 383 |
| ACC TCT GCA GAT GAT A<br>Thr Ser Ala Asp Asp<br>         130 | 399 |

(2) INFORMATION FOR SEQ ID NO:2:

(i) SEQUENCE CHARACTERISTICS:
        (A) LENGTH: 132 amino acids
        (B) TYPE: amino acid
        (D) TOPOLOGY: linear (ii) MOLECULE TYPE: protein (xi) SEQUENCE DESCRIPTION: SEQ ID NO:2:

Ala Val Asp Glu Asp Asp Glu Asp Glu Glu Glu Gly Glu Glu Val Val
  1             5                   10                15

Glu Asp Arg Asp Tyr Tyr Tyr Asp Thr Phe Lys Gly Asp Asp Tyr Asn
           20                   25               30

Glu Glu Asn Pro Thr Glu Pro Gly Ser Asp Gly Thr Met Ser Asp Lys
        35                 40                45

Glu Ile Thr His Asp Val Lys Ala Val Cys Ser Gln Glu Ala Met Thr
   50                55               60

Gly Pro Cys Arg Ala Val Met Pro Arg Trp Tyr Phe Asp Leu Ser Lys
 65               70               75               80

Gly Lys Cys Val Arg Phe Ile Tyr Gly Gly Cys Gly Gly Asn Arg Asn
           85                 90               95

Asn Phe Glu Ser Glu Asp Tyr Cys Met Ala Val Cys Lys Ala Met Ile
        100                105             110

Pro Pro Thr Pro Leu Pro Thr Asn Asp Val Asp Val Tyr Phe Glu Thr
       115              120            125

Ser Ala Asp Asp
    130

(2) INFORMATION FOR SEQ ID NO:3:

(i) SEQUENCE CHARACTERISTICS:
            (A) LENGTH: 235 base pairs
            (B) TYPE: nucleic acid
            (C) STRANDEDNESS: single
            (D) TOPOLOGY: linear (ix) FEATURE:
            (A) NAME/KEY: CDS
            (B) LOCATION: 77..235

(xi) SEQUENCE DESCRIPTION: SEQ ID NO:3:

```
GAATTCCATT CAAGAATAGT TCAAACAAGA AGATTACAAA CTATCAATTT CATACACAAT      60

ATAAACGACC AAAAGA ATG AAG GCT GTT TTC TTG GTT TTG TCC TTG ATC        109
               Met Lys Ala Val Phe Leu Val Leu Ser Leu Ile
                 1               5                  10

GGA TTC TGC TGG GCC CAA CCA GTC ACT GGC GAT GAA TCA TCT GTT GAG      157
Gly Phe Cys Trp Ala Gln Pro Val Thr Gly Asp Glu Ser Ser Val Glu
             15                  20                  25

ATT CCG GAA GAG TCT CTG ATC ATC GCT GAA AAC ACC ACT TTG GCT AAC      205
Ile Pro Glu Glu Ser Leu Ile Ile Ala Glu Asn Thr Thr Leu Ala Asn
 30                  35                  40

GTC GCC ATG GCT GAG AGA TTG GAG AAG AGA                              235
Val Ala Met Ala Glu Arg Leu Glu Lys Arg
         45                  50
```

(2) INFORMATION FOR SEQ ID NO:4:

(i) SEQUENCE CHARACTERISTICS:
            (A) LENGTH: 53 amino acids
            (B) TYPE: amino acid
            (D) TOPOLOGY: linear (ii) MOLECULE TYPE: protein (xi) SEQUENCE DESCRIPTION: SEQ ID NO:4:

```
Met Lys Ala Val Phe Leu Val Leu Ser Leu Ile Gly Phe Cys Trp Ala
  1               5                  10                  15

Gln Pro Val Thr Gly Asp Glu Ser Ser Val Glu Ile Pro Glu Glu Ser
                 20                  25                  30

Leu Ile Ile Ala Glu Asn Thr Thr Leu Ala Asn Val Ala Met Ala Glu
             35                  40                  45

Arg Leu Glu Lys Arg
     50
```

(2) INFORMATION FOR SEQ ID NO:5:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (vii) IMMEDIATE SOURCE:
            (B) CLONE: ZC4792

(xi) SEQUENCE DESCRIPTION: SEQ ID NO:5:

```
GTTGTTGCTG TTGCCTCCGC AGCCTCCGTA                                      30
```

(2) INFORMATION FOR SEQ ID NO:6:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (vii) IMMEDIATE SOURCE:

(B) CLONE: M-1251

(xi) SEQUENCE DESCRIPTION: SEQ ID NO:6:

GCTGAGAGAT TGGGAGAAGA GAGCTGTCTG CTCCCAGGAG GC          42

(2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (vii) IMMEDIATE SOURCE:
        (B) CLONE: M-1252

(xi) SEQUENCE DESCRIPTION: SEQ ID NO:7:

AGTTGGTCTA GATTACGCTT TACACACAGC CATAC                  35

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (vii) IMMEDIATE SOURCE:
        (B) CLONE: NOR-1478

(xi) SEQUENCE DESCRIPTION: SEQ ID NO:8:

GTAAAACGAC GGCCAGT                                      17

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (vii) IMMEDIATE SOURCE:
        (B) CLONE: NOR-2523

(xi) SEQUENCE DESCRIPTION: SEQ ID NO:9:

TCTCTTCTCC AATCTCTCAG C                                 21

(2) INFORMATION FOR SEQ ID NO:10:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (vii) IMMEDIATE SOURCE:
        (B) CLONE: M-1249

(xi) SEQUENCE DESCRIPTION: SEQ ID NO:10:

GCTGAGAGAT TGGAGAAGAG AGATGTCAAA GCTGTCTGCT CCC          43

(2) INFORMATION FOR SEQ ID NO:11:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (vii) IMMEDIATE SOURCE:

(B) CLONE: M-1250

(xi) SEQUENCE DESCRIPTION: SEQ ID NO:11:

| | |
|---|---:|
| GCTGAGAGAT TGGAGAAGAG AGAAGTCTGC TCCCAGGAGG C | 41 |

(2) INFORMATION FOR SEQ ID NO:12:

(i) SEQUENCE CHARACTERISTICS:
        (A) LENGTH: 3725 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Homo sapiens (vii) IMMEDIATE SOURCE:
        (B) CLONE: APPH (ix) FEATURE:
        (A) NAME/KEY: CDS
        (B) LOCATION: 73..2364

(xi) SEQUENCE DESCRIPTION: SEQ ID NO:12:

| | |
|---|---:|
| GTCGCGGTGT GCTAAGCGAG GAGTCCGAGT GTGTGAGCTT GAGAGCCGCG CGCTAGAGCG | 60 |
| ACCCGGCGAG GG ATG GCG GCC ACC GGG ACC GCG GCC GCC GCA GCC ACG<br>              Met Ala Ala Thr Gly Thr Ala Ala Ala Ala Ala Thr<br>               1              5                     10 | 108 |
| GGC AGG CTC CTG CTT CTG CTG CTG GTG GGG CTC ACG GCG CCT GCC TTG<br>Gly Arg Leu Leu Leu Leu Leu Leu Val Gly Leu Thr Ala Pro Ala Leu<br>             15                   20                 25 | 156 |
| GCG CTG GCC GGC TAC ATC GAG GCT CTT GCA GCC AAT GCC GGA ACA GGA<br>Ala Leu Ala Gly Tyr Ile Glu Ala Leu Ala Ala Asn Ala Gly Thr Gly<br>     30                   35                 40 | 204 |
| TTT GCT GTT GCT GAG CCT CAA ATC GCA ATG TTT TGT GGG AAG TTA AAT<br>Phe Ala Val Ala Glu Pro Gln Ile Ala Met Phe Cys Gly Lys Leu Asn<br>45                   50                 55                 60 | 252 |
| ATG CAT GTG AAC ATT CAG ACT GGG AAA TGG GAA CCT GAT CCA ACA GGC<br>Met His Val Asn Ile Gln Thr Gly Lys Trp Glu Pro Asp Pro Thr Gly<br>             65                   70                 75 | 300 |
| ACC AAG AGC TGC TTT GAA ACA AAA GAA GAA GTT CTT CAG TAC TGT CAG<br>Thr Lys Ser Cys Phe Glu Thr Lys Glu Glu Val Leu Gln Tyr Cys Gln<br>                80                   85                 90 | 348 |
| GAG ATG TAT CCA GAG CTA CAG ATC ACA AAT GTG ATG GAG GCA AAC CAG<br>Glu Met Tyr Pro Glu Leu Gln Ile Thr Asn Val Met Glu Ala Asn Gln<br>                   95                   100                105 | 396 |
| CGG GTT AGT ATT GAC AAC TGG TGC CGG AGG GAC AAA AAG CAA TGC AAG<br>Arg Val Ser Ile Asp Asn Trp Cys Arg Arg Asp Lys Lys Gln Cys Lys<br>      110                   115                 120 | 444 |
| AGT CGC TTT GTT ACA CCT TTC AAG TGT CTC GTG GGT GAA TTT GTA AGT<br>Ser Arg Phe Val Thr Pro Phe Lys Cys Leu Val Gly Glu Phe Val Ser<br>125                 130                 135                 140 | 492 |
| GAT GTC CTG CTA GTT CCA GAA AAG TGC CAG TTT TTC CAC AAA GAG CGG<br>Asp Val Leu Leu Val Pro Glu Lys Cys Gln Phe Phe His Lys Glu Arg<br>                   145                 150                 155 | 540 |
| ATG GAG GTG TGT GAG AAT CAC CAG CAC TGG CAC ACG GTA GTC AAA GAG<br>Met Glu Val Cys Glu Asn His Gln His Trp His Thr Val Val Lys Glu<br>              160                   165                 170 | 588 |
| GCA TGT CTG ACT CAG GGA ATG ACC TTA TAT AGC TAC GGC ATG CTG CTC<br>Ala Cys Leu Thr Gln Gly Met Thr Leu Tyr Ser Tyr Gly Met Leu Leu<br>             175                   180                 185 | 636 |
| CCA TGT GGG GTA GAC CAG TTC CAT GGC ACT GAA TAT GTG TGC TGC CCT | 684 |

```
        Pro Cys Gly Val Asp Gln Phe His Gly Thr Glu Tyr Val Cys Cys Pro
            190                 195                 200

CAG ACA AAG ATT ATT GGA TCT GTG TCA AAA GAA GAG GAA GAG GAA GAT         732
Gln Thr Lys Ile Ile Gly Ser Val Ser Lys Glu Glu Glu Glu Glu Asp
205                 210                 215                 220

GAA GAG GAA GAG GAA GAG GAA GAT GAA GAG GAA GAC TAT GAT GTT TAT         780
Glu Glu Glu Glu Glu Glu Glu Asp Glu Glu Glu Asp Tyr Asp Val Tyr
                    225                 230                 235

AAA AGT GAA TTT CCT ACT GAA GCA GAT CTG GAA GAC TTC ACA GAA GCA         828
Lys Ser Glu Phe Pro Thr Glu Ala Asp Leu Glu Asp Phe Thr Glu Ala
                240                 245                 250

GCT GTG GAT GAG GAT GAT GAG GAT GAG GAA GAA GGG GAG GAA GTG GTG         876
Ala Val Asp Glu Asp Asp Glu Asp Glu Glu Glu Gly Glu Glu Val Val
                    255                 260                 265

GAG GAC CGA GAT TAC TAC TAT GAC ACC TTC AAA GGA GAT GAC TAC AAT         924
Glu Asp Arg Asp Tyr Tyr Tyr Asp Thr Phe Lys Gly Asp Asp Tyr Asn
270                 275                 280

GAG GAG AAT CCT ACT GAA CCC GGC AGC GAC GGC ACC ATG TCA GAC AAG         972
Glu Glu Asn Pro Thr Glu Pro Gly Ser Asp Gly Thr Met Ser Asp Lys
285                 290                 295                 300

GAA ATT ACT CAT GAT GTC AAA GCT GTC TGC TCC CAG GAG GCG ATG ACG        1020
Glu Ile Thr His Asp Val Lys Ala Val Cys Ser Gln Glu Ala Met Thr
                    305                 310                 315

GGG CCC TGC CGG GCC GTG ATG CCT CGT TGG TAC TTC GAC CTC TCC AAG        1068
Gly Pro Cys Arg Ala Val Met Pro Arg Trp Tyr Phe Asp Leu Ser Lys
                320                 325                 330

GGA AAG TGC GTG CGC TTT ATA TAT GGT GGC TGC GGC GGC AAC AGG AAC        1116
Gly Lys Cys Val Arg Phe Ile Tyr Gly Gly Cys Gly Gly Asn Arg Asn
                    335                 340                 345

AAT TTT GAG TCT GAG GAT TAT TGT ATG GCT GTG TGT AAA GCG ATG ATT        1164
Asn Phe Glu Ser Glu Asp Tyr Cys Met Ala Val Cys Lys Ala Met Ile
350                 355                 360

CCT CCA ACT CCT CTG CCA ACC AAT GAT GTT GAT GTG TAT TTC GAG ACC        1212
Pro Pro Thr Pro Leu Pro Thr Asn Asp Val Asp Val Tyr Phe Glu Thr
365                 370                 375                 380

TCT GCA GAT GAT AAT GAG CAT GCT CGC TTC CAG AAG GCT AAG GAG CAG        1260
Ser Ala Asp Asp Asn Glu His Ala Arg Phe Gln Lys Ala Lys Glu Gln
                    385                 390                 395

CTG GAG ATT CGG CAC CGC AAC CGA ATG GAC AGG GTA AAG AAG GAA TGG        1308
Leu Glu Ile Arg His Arg Asn Arg Met Asp Arg Val Lys Lys Glu Trp
                400                 405                 410

GAA GAG GCA GAG CTT CAA GCT AAG AAC CTC CCC AAA GCA GAG AGG CAG        1356
Glu Glu Ala Glu Leu Gln Ala Lys Asn Leu Pro Lys Ala Glu Arg Gln
                    415                 420                 425

ACT CTG ATT CAG CAC TTC CAA GCC ATG GTT AAA GCT TTA GAG AAG GAA        1404
Thr Leu Ile Gln His Phe Gln Ala Met Val Lys Ala Leu Glu Lys Glu
        430                 435                 440

GCA GCC AGT GAG AAG CAG CAG CTG GTG GAG ACC CAC CTG GCC CGA GTG        1452
Ala Ala Ser Glu Lys Gln Gln Leu Val Glu Thr His Leu Ala Arg Val
445                 450                 455                 460

GAA GCT ATG CTG AAT GAC CGC CGT CGG ATG GCT CTG GAG AAC TAC CTG        1500
Glu Ala Met Leu Asn Asp Arg Arg Arg Met Ala Leu Glu Asn Tyr Leu
                465                 470                 475

GCT GCC TTG CAG TCT GAC CCG CCA CGG CCT CAT CGC ATT CTC CAG GCC        1548
Ala Ala Leu Gln Ser Asp Pro Pro Arg Pro His Arg Ile Leu Gln Ala
                    480                 485                 490

TTA CGG CGT TAT GTC CGT GCT GAG AAC AAA GAT CGC TTA CAT ACC ATC        1596
Leu Arg Arg Tyr Val Arg Ala Glu Asn Lys Asp Arg Leu His Thr Ile
                495                 500                 505

CGT CAT TAC CAG CAT GTG TTG GCT GTT GAC CCA GAA AAG GCG GCC CAG        1644
```

```
Arg His Tyr Gln His Val Leu Ala Val Asp Pro Glu Lys Ala Ala Gln
510                 515                 520

ATG AAA TCC CAG GTG ATG ACA CAT CTC CAC GTG ATT GAA GAA AGG AGG   1692
Met Lys Ser Gln Val Met Thr His Leu His Val Ile Glu Glu Arg Arg
525                 530                 535                 540

AAC CAA ATC CTC TCT CTG CTC TAC AAA GTA CCT TAT GTA GCC CAA GAA   1740
Asn Gln Ile Leu Ser Leu Leu Tyr Lys Val Pro Tyr Val Ala Gln Glu
                545                 550                 555

ATT CAA GAG GAA ATT GAT GAG CTC CTT CAG GAG CAG CGT GCA GAT ATG   1788
Ile Gln Glu Glu Ile Asp Glu Leu Leu Gln Glu Gln Arg Ala Asp Met
                560                 565                 570

GAC CAG TTC ACT GCC TCA ATC TCA GAG ACC CCT GTG GAC GTC CGG GTG   1836
Asp Gln Phe Thr Ala Ser Ile Ser Glu Thr Pro Val Asp Val Arg Val
        575                 580                 585

AGC TCT GAG GAG AGT GAG GAG ATC CCA CCG TTC CAC CCC TTC CAC CCC   1884
Ser Ser Glu Glu Ser Glu Glu Ile Pro Pro Phe His Pro Phe His Pro
        590                 595                 600

TTC CCA GCC CTA CCT GAG AAC GAA GAC ACT CAG CCG GAG TTG TAC CAC   1932
Phe Pro Ala Leu Pro Glu Asn Glu Asp Thr Gln Pro Glu Leu Tyr His
605                 610                 615                 620

CCA ATG AAA AAA GGA TCT GGA GTG GGA GAG CAG GAT GGG GGA CTG ATC   1980
Pro Met Lys Lys Gly Ser Gly Val Gly Glu Gln Asp Gly Gly Leu Ile
                625                 630                 635

GGT GCC GAA GAG AAA GTG ATT AAC AGT AAG AAT AAA GTG GAT GAA AAC   2028
Gly Ala Glu Glu Lys Val Ile Asn Ser Lys Asn Lys Val Asp Glu Asn
                640                 645                 650

ATG GTC ATT GAC GAG ACT CTG GAT GTT AAG GAA ATG ATT TTC AAT GCC   2076
Met Val Ile Asp Glu Thr Leu Asp Val Lys Glu Met Ile Phe Asn Ala
        655                 660                 665

GAG AGA GTT GGA GGC CTC GAG GAA GAG CGG GAA TCC GTG GGC CCA CTG   2124
Glu Arg Val Gly Gly Leu Glu Glu Glu Arg Glu Ser Val Gly Pro Leu
        670                 675                 680

CGG GAG GAC TTC AGT CTG AGT AGC AGT GCT CTC ATT GGC CTG CTG GTC   2172
Arg Glu Asp Phe Ser Leu Ser Ser Ser Ala Leu Ile Gly Leu Leu Val
685                 690                 695                 700

ATC GCA GTG GCC ATT GCC ACG GTC ATC GTC ATC AGC CTG GTG ATG CTG   2220
Ile Ala Val Ala Ile Ala Thr Val Ile Val Ile Ser Leu Val Met Leu
                705                 710                 715

AGG AAG AGG CAG TAT GGC ACC ATC AGC CAC GGG ATC GTG GAG GTT GAT   2268
Arg Lys Arg Gln Tyr Gly Thr Ile Ser His Gly Ile Val Glu Val Asp
                720                 725                 730

CCA ATG CTC ACC CCA GAA GAG CGT CAC CTG AAC AAG ATG CAG AAC CAT   2316
Pro Met Leu Thr Pro Glu Glu Arg His Leu Asn Lys Met Gln Asn His
        735                 740                 745

GGC TAT GAG AAC CCC ACC TAC AAA TAC CTG GAG CAG ATG CAG ATT TAGGTGGC 2371
Gly Tyr Glu Asn Pro Thr Tyr Lys Tyr Leu Glu Gln Met Gln Ile
        750                 755                 760

GGAGCGCGGC AGCCCTGGCG GAGGGATGCA GGTGGGCCGG AAGATCCCAC GATTCCGATC     2431

GACTGCCAAG CAGCAGCCGC TGCCAGGGGC TGCGTCTGAC ATCCTGACCT CCTGGACTGT     2491

AGGACTATAT AAAGTACTAC TGTAGAACTG CAATTTCCAT TCTTTTAAAT GGGTGAAAAA     2551

TGGTAATATA ACAATATATG ATATATAAAC CTTAAATGAA AAAAATGATC TATTGCAGAT     2611

ATTTGATGTA GTTTTCTTTT TTAAATTAAT CAGAAACCCC ACTTCCATTG TATTGTCTGA     2671

CACATGCTCT CAATATATAA TAAATGGGAA ATGTCGATTT TCAATAATAG ACTTATATGC     2731

AGGCTGTCGT TCCGGTTATG TTGTGTAAGT CAACTCTTCA GCCTCATTCA CTGTCCTGGC     2791

TTTTATTTAA AGAAAAAAAA GGCAGTATTC CCTTTTTAAA TGAGCTTTCA GGAAGTTGCT     2851

GAGAAATGGG GTGGAATAGG GAACTGTAAT GGCCACTGAA GCACGTGAGA GACCCTCGCA     2911
```

-continued

```
AAATGATGTG AAAGGACCAG TTTCTTGAAG TCCAGTGTTT CCACGGCTGG ATACCTGTGT    2971

GTCTCCATAA AAGTCCTGTC ACCAAGGACG TTAAAGGCAT TTTATTCCAG CGTCTTCTAG    3031

AGAGCTTAGT GTATACAGAT GAGGGTGTCC GCTGCTGCTT TCCTTCGGAA TCCAGTGCTT    3091

CCACAGAGAT TAGCCTGTAG CTTATATTTG ACATTCTTCA CTGTCTGTTG TTTACCTACC    3151

GTAGCTTTTT ACCGTTCACT TCCCCTTCCA ACTATGTCCA GATGTGCAGG CTCCTCCTCT    3211

CTGGACTTTC TCCAAAGGCA CTGACCCTCG GCCTCTACTT TGTCCCCTCA CCTCCACCCC    3271

CTCCTGTCAC CGGCCTTGTG ACATTCACTC AGAGAAGACC ACACCAAGGA GGGGCCGCGG    3331

CTGGCCCAGG AGAGAACACG GGGAGGTTTG TTTGTGTGAA AGGAAAGTAG TCCAGGCTGT    3391

CCCTGAAACT GAGTCTGTGG ACACTGTGGA AAGCTTTGAA CAATTGTGTT TTCGTCACAG    3451

GAGTCTTTGT AATGCTTGTA CAGTTGATGT CGATGCTCAC TGCTTCTGCT TTTTCTTTCT    3511

TTTTATTTTA AAAAATCTGA AGGTTCTGGT AACCTGTGGT GTATTTTTAT TTTCCTGTGA    3571

CTGTTTTTGT TTTGTTTTTT TCCTTTTTCC TCCCCTTTAG CCCTATTCAT GTCTCTACCC    3631

ACTATGCACA GATTAAACTT CACCTACAAA CTCCTTAATA TGATCTGTGG AGAATGTACA    3691

CAGTTTAAAC ACATCAATAA ATACTTTAAC TTCC                                3725
```

(2) INFORMATION FOR SEQ ID NO:13:

(i) SEQUENCE CHARACTERISTICS:
        (A) LENGTH: 763 amino acids
        (B) TYPE: amino acid
        (D) TOPOLOGY: linear (ii) MOLECULE TYPE: protein (xi) SEQUENCE DESCRIPTION: SEQ ID NO:13:

```
Met Ala Ala Thr Gly Thr Ala Ala Ala Ala Thr Gly Arg Leu Leu
 1               5                  10                  15

Leu Leu Leu Leu Val Gly Leu Thr Ala Pro Ala Leu Ala Leu Ala Gly
                20                  25                  30

Tyr Ile Glu Ala Leu Ala Ala Asn Ala Gly Thr Gly Phe Ala Val Ala
            35                  40                  45

Glu Pro Gln Ile Ala Met Phe Cys Gly Lys Leu Asn Met His Val Asn
        50                  55                  60

Ile Gln Thr Gly Lys Trp Glu Pro Asp Pro Thr Gly Thr Lys Ser Cys
65                  70                  75                  80

Phe Glu Thr Lys Glu Glu Val Leu Gln Tyr Cys Gln Glu Met Tyr Pro
                85                  90                  95

Glu Leu Gln Ile Thr Asn Val Met Glu Ala Asn Gln Arg Val Ser Ile
            100                 105                 110

Asp Asn Trp Cys Arg Arg Asp Lys Lys Gln Cys Lys Ser Arg Phe Val
        115                 120                 125

Thr Pro Phe Lys Cys Leu Val Gly Glu Phe Val Ser Asp Val Leu Leu
    130                 135                 140

Val Pro Glu Lys Cys Gln Phe Phe His Lys Glu Arg Met Glu Val Cys
145                 150                 155                 160

Glu Asn His Gln His Trp His Thr Val Val Lys Glu Ala Cys Leu Thr
                165                 170                 175

Gln Gly Met Thr Leu Tyr Ser Tyr Gly Met Leu Leu Pro Cys Gly Val
            180                 185                 190

Asp Gln Phe His Gly Thr Glu Tyr Val Cys Cys Pro Gln Thr Lys Ile
        195                 200                 205
```

-continued

```
Ile Gly Ser Val Ser Lys Glu Glu Glu Asp Glu Glu Glu
210             215             220
Glu Glu Glu Asp Glu Glu Asp Tyr Asp Val Tyr Lys Ser Glu Phe
225             230             235             240
Pro Thr Glu Ala Asp Leu Glu Asp Phe Thr Glu Ala Ala Val Asp Glu
                245                 250                 255
Asp Asp Glu Asp Glu Glu Glu Gly Glu Glu Val Val Glu Asp Arg Asp
            260                 265                 270
Tyr Tyr Tyr Asp Thr Phe Lys Gly Asp Asp Tyr Asn Glu Glu Asn Pro
        275                 280                 285
Thr Glu Pro Gly Ser Asp Gly Thr Met Ser Asp Lys Glu Ile Thr His
    290                 295                 300
Asp Val Lys Ala Val Cys Ser Gln Glu Ala Met Thr Gly Pro Cys Arg
305                 310                 315                 320
Ala Val Met Pro Arg Trp Tyr Phe Asp Leu Ser Lys Gly Lys Cys Val
                325                 330                 335
Arg Phe Ile Tyr Gly Gly Cys Gly Asn Arg Asn Asn Phe Glu Ser
            340                 345                 350
Glu Asp Tyr Cys Met Ala Val Cys Lys Ala Met Ile Pro Thr Pro
        355                 360                 365
Leu Pro Thr Asn Asp Val Asp Val Tyr Phe Glu Thr Ser Ala Asp Asp
    370                 375                 380
Asn Glu His Ala Arg Phe Gln Lys Ala Lys Glu Gln Leu Glu Ile Arg
385                 390                 395                 400
His Arg Asn Arg Met Asp Arg Val Lys Lys Glu Trp Glu Ala Glu
                405                 410                 415
Leu Gln Ala Lys Asn Leu Pro Lys Ala Glu Arg Gln Thr Leu Ile Gln
            420                 425                 430
His Phe Gln Ala Met Val Lys Ala Leu Glu Lys Glu Ala Ala Ser Glu
        435                 440                 445
Lys Gln Gln Leu Val Glu Thr His Leu Ala Arg Val Glu Ala Met Leu
    450                 455                 460
Asn Asp Arg Arg Arg Met Ala Leu Glu Asn Tyr Leu Ala Ala Leu Gln
465                 470                 475                 480
Ser Asp Pro Pro Arg Pro His Arg Ile Leu Gln Ala Leu Arg Arg Tyr
                485                 490                 495
Val Arg Ala Glu Asn Lys Asp Arg Leu His Thr Ile Arg His Tyr Gln
            500                 505                 510
His Val Leu Ala Val Asp Pro Glu Lys Ala Ala Gln Met Lys Ser Gln
        515                 520                 525
Val Met Thr His Leu His Val Ile Glu Glu Arg Arg Asn Gln Ile Leu
    530                 535                 540
Ser Leu Leu Tyr Lys Val Pro Tyr Val Ala Gln Glu Ile Gln Glu Glu
545                 550                 555                 560
Ile Asp Glu Leu Leu Gln Glu Gln Arg Ala Asp Met Asp Gln Phe Thr
                565                 570                 575
Ala Ser Ile Ser Glu Thr Pro Val Asp Val Arg Val Ser Ser Glu Glu
            580                 585                 590
Ser Glu Glu Ile Pro Pro Phe His Pro Phe His Pro Phe Pro Ala Leu
        595                 600                 605
Pro Glu Asn Glu Asp Thr Gln Pro Glu Leu Tyr His Pro Met Lys Lys
    610                 615                 620
Gly Ser Gly Val Gly Glu Gln Asp Gly Gly Leu Ile Gly Ala Glu Glu
625                 630                 635                 640
```

```
Lys Val Ile Asn Ser Lys Asn Lys Val Asp Glu Asn Met Val Ile Asp
                645                 650                 655

Glu Thr Leu Asp Val Lys Glu Met Ile Phe Asn Ala Glu Arg Val Gly
            660                 665                 670

Gly Leu Glu Glu Glu Arg Glu Ser Val Gly Pro Leu Arg Glu Asp Phe
        675                 680                 685

Ser Leu Ser Ser Ser Ala Leu Ile Gly Leu Leu Val Ile Ala Val Ala
        690                 695                 700

Ile Ala Thr Val Ile Val Ile Ser Leu Val Met Leu Arg Lys Arg Gln
705                 710                 715                 720

Tyr Gly Thr Ile Ser His Gly Ile Val Glu Val Asp Pro Met Leu Thr
                725                 730                 735

Pro Glu Glu Arg His Leu Asn Lys Met Gln Asn His Gly Tyr Glu Asn
            740                 745                 750

Pro Thr Tyr Lys Tyr Leu Glu Gln Met Gln Ile
        755                 760
```

(2) INFORMATION FOR SEQ ID NO:14:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (vii) IMMEDIATE SOURCE:
        (B) CLONE: Primer 1

(xi) SEQUENCE DESCRIPTION: SEQ ID NO:14:

GCTGAGAGAT TGGAGAAGAG AGAGGTGTGC TCTGAAC          37

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (vii) IMMEDIATE SOURCE:
        (B) CLONE: Primer 2

(xi) SEQUENCE DESCRIPTION: SEQ ID NO:15:

CTGCTATCTA GATTAGGCGC TGCCACACAC GGC          33

(2) INFORMATION FOR SEQ ID NO:16:

(i) SEQUENCE CHARACTERISTICS:
        (A) LENGTH: 168 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Homo sapiens (vii) IMMEDIATE SOURCE:
        (B) CLONE: APP (ix) FEATURE:
        (A) NAME/KEY: CDS
        (B) LOCATION: 1..168

(xi) SEQUENCE DESCRIPTION: SEQ ID NO:16:

```
GAG GTG TGC TCT GAA CAA GCC GAG ACG GGG CCG TGC CGA GCA ATG ATC        48
Glu Val Cys Ser Glu Gln Ala Glu Thr Gly Pro Cys Arg Ala Met Ile
 1               5                  10                  15

TCC CGC TGG TAC TTT GAT GTG ACT GAA GGG AAG TGT GCC CCA TTC TTT        96
Ser Arg Trp Tyr Phe Asp Val Thr Glu Gly Lys Cys Ala Pro Phe Phe
                20                  25                  30

TAC GGC GGA TGT GGC GGC AAC CGG AAC AAC TTT GAC ACA GAA GAG TAC       144
Tyr Gly Gly Cys Gly Gly Asn Arg Asn Asn Phe Asp Thr Glu Glu Tyr
         35                  40                  45

TGC ATG GCC GTG TGT GGC AGC GCC                                       168
Cys Met Ala Val Cys Gly Ser Ala
     50                  55

(2) INFORMATION FOR SEQ ID NO:17:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO:17:

Glu Val Cys Ser Glu Gln Ala Glu Thr Gly Pro Cys Arg Ala Met Ile
 1               5                  10                  15

Ser Arg Trp Tyr Phe Asp Val Thr Glu Gly Lys Cys Ala Pro Phe Phe
                20                  25                  30

Tyr Gly Gly Cys Gly Gly Asn Arg Asn Asn Phe Asp Thr Glu Glu Tyr
         35                  40                  45

Cys Met Ala Val Cys Gly Ser Ala
     50                  55

(2) INFORMATION FOR SEQ ID NO:18:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 1..4
        (D) OTHER INFORMATION: /label= Ala-1
            /note= "Amino-terminal alanine residue is capped
            with a methoxysuccinyl gr..."

(ix) FEATURE:
        (A) NAME/KEY: Modified-site
        (B) LOCATION: 1..4
        (D) OTHER INFORMATION: /label= Val-4
            /note= "Carboxyl-terminal valine residue is capped
            with p-nitroznilide"

(xi) SEQUENCE DESCRIPTION: SEQ ID NO:18:

Ala Ala Pro Val
 1

(2) INFORMATION FOR SEQ ID NO:19:

(i) SEQUENCE CHARACTERISTICS:
        (A) LENGTH: 4 amino acids
        (B) TYPE: amino acid
        (D) TOPOLOGY: linear (ii) MOLECULE TYPE: peptide
```

```
    (v) FRAGMENT TYPE: internal (ix) FEATURE:
        (A) NAME/KEY: Modified-site
        (B) LOCATION: 1..4
        (D) OTHER INFORMATION: /label= ALA-1
             /note= "Amino terminal alanine residue is capped
             with a succinyl group"

(ix) FEATURE:
        (A) NAME/KEY: Modified-site
        (B) LOCATION: 1..4
        (D) OTHER INFORMATION: /label= Phe-4
             /note= "Carboxyl-terminal phenylalanine resudue is
             capped with p-nitroanil..."

(xi) SEQUENCE DESCRIPTION: SEQ ID NO:19:

Ala Ala Pro Phe
```